US009787815B2

United States Patent
Erickson et al.

(10) Patent No.: US 9,787,815 B2
(45) Date of Patent: *Oct. 10, 2017

(54) SMARTPHONE-BASED APPARATUS AND METHOD

(71) Applicant: Cornell University, Ithaca, NY (US)

(72) Inventors: David Erickson, Ithaca, NY (US); Seoho Lee, Ithaca, NY (US); Dakota O'Dell, Ithaca, NY (US); Saurabh Mehta, Ithaca, NY (US); Vlad-Victor Oncescu, Ithaca, NY (US); Matthew Mancuso, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/804,386

(22) Filed: Jul. 21, 2015

(65) Prior Publication Data

US 2016/0080548 A1    Mar. 17, 2016

Related U.S. Application Data

(63) Continuation-in-part of application No. PCT/US2014/012263, filed on Jan. 21, 2014.
(Continued)

(51) Int. Cl.
*H04M 1/725* (2006.01)
*G01N 33/487* (2006.01)
(Continued)

(52) U.S. Cl.
CPC ........ *H04M 1/72527* (2013.01); *G01N 21/78* (2013.01); *G01N 21/80* (2013.01);
(Continued)

(58) Field of Classification Search
CPC ............ H04M 1/72527; H04M 1/0264; G01N 21/8483; G01N 33/48785; G01N 21/80;
(Continued)

(56) References Cited

U.S. PATENT DOCUMENTS 7,428,016 B2 *  9/2008  Takenaka ................ H04M 1/22
                                                        348/371
2003/0050537 A1  3/2003  Wessel
(Continued)

OTHER PUBLICATIONS

International Search Report and Written Opinion Form PCT/ISA/220, International Application No. PCT/US2014/012263, pp. 1-11, International Filing Date Jan. 21, 2014.

*Primary Examiner* — Andrew Wendell
(74) *Attorney, Agent, or Firm* — Bond, Schoeneck & King, PLLC; William Greener; Erin Phillips

(57) ABSTRACT

A method for obtaining a point-of-collection, selected quantitative indicia of an analyte on a test strip using a smartphone involves imaging a test strip on which a colorimetric reaction of a target sample has occurred due to test strip illumination by the smartphone. The smartphone includes a smartphone app and a smartphone accessory that provides an external environment-independent/internal light-free, imaging environment independent of the smartphone platform being used. The result can then be presented quantitatively or turned into a more consumer-friendly measurement (positive, negative, above average, etc.), displayed to the user, stored for later use, and communicated to a location where practitioners can provide additional review. Additionally, social media integration can allow for device results to be broadcast to specific audiences, to compare healthy living with others, to compete in health based games, create mappings, and other applications.

26 Claims, 15 Drawing Sheets

Related U.S. Application Data

(60) Provisional application No. 61/754,733, filed on Jan. 21, 2013, provisional application No. 61/810,766, filed on Apr. 11, 2013, provisional application No. 61/892,154, filed on Oct. 17, 2013, provisional application No. 62/142,513, filed on Apr. 3, 2015.

(51) Int. Cl.
| | | |
|---|---|---|
| *G01N 21/77* | (2006.01) | |
| *G01N 21/78* | (2006.01) | |
| *G01N 21/80* | (2006.01) | |
| *G01N 21/84* | (2006.01) | |
| *H04N 5/225* | (2006.01) | |

(52) U.S. Cl.
CPC ... *G01N 21/8483* (2013.01); *G01N 33/48785* (2013.01); *H04N 5/2251* (2013.01); *G01N 2021/7759* (2013.01); *G01N 2201/0221* (2013.01); *G01N 2201/062* (2013.01); *G01N 2201/127* (2013.01)

(58) Field of Classification Search
CPC ........... G01N 21/78; G01N 2201/0221; G01N 2201/062; G01N 2021/7759; G01N 2201/127; G06K 9/4652; G06K 9/4633; H04N 5/2256; H04N 5/2252
See application file for complete search history.

(56) References Cited

U.S. PATENT DOCUMENTS

| | | | |
|---|---|---|---|
| 2006/0222567 A1 | 10/2006 | Kloepfer et al. | |
| 2006/0292039 A1 | 12/2006 | Ilda | |
| 2009/0135287 A1* | 5/2009 | Yang | G02B 7/02 348/335 |
| 2011/0038765 A1 | 2/2011 | Drucker et al. | |
| 2012/0293802 A1* | 11/2012 | Ozin | G01D 5/28 356/402 |
| 2012/0320626 A1* | 12/2012 | Quilici | F21S 8/04 362/606 |
| 2013/0267032 A1* | 10/2013 | Tsai | G01N 21/78 436/95 |
| 2014/0072189 A1* | 3/2014 | Jena | G01N 21/8483 382/128 |
| 2015/0338387 A1* | 11/2015 | Ehrenkranz | A61B 5/6898 424/450 |
| 2015/0359458 A1* | 12/2015 | Erickson | G01N 33/52 455/557 |

* cited by examiner

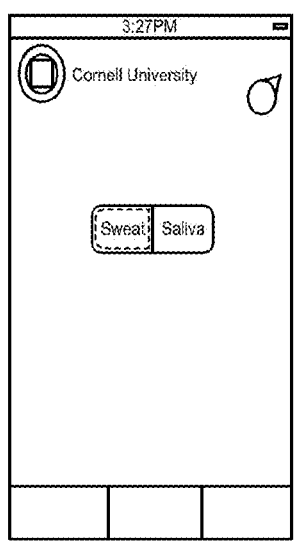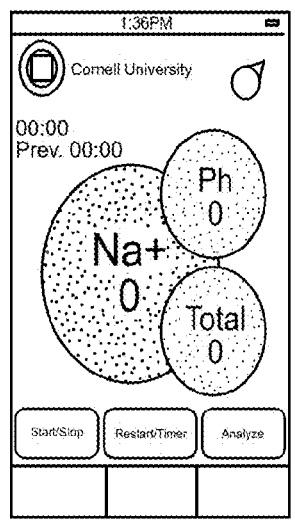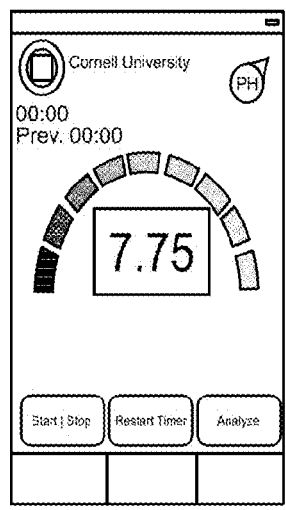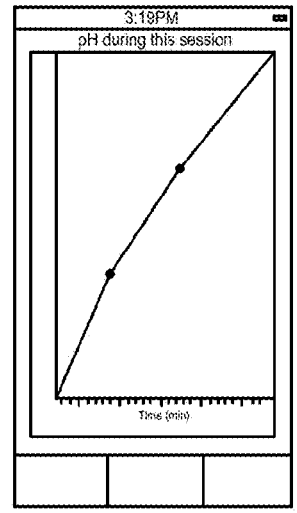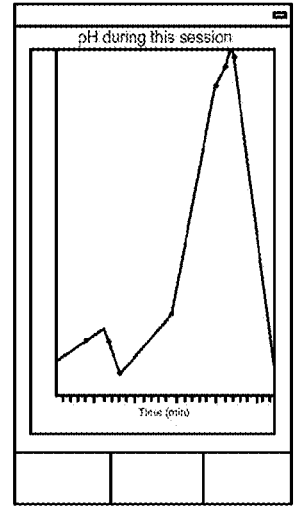
FIG. 3A          FIG. 3B          FIG. 3C

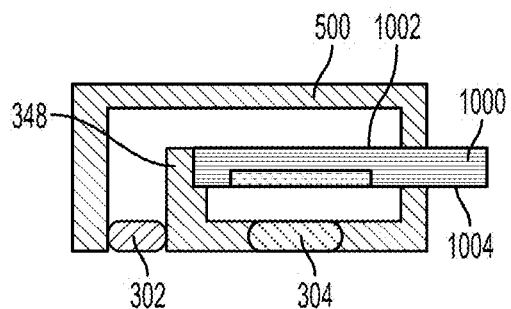
FIG. 4A
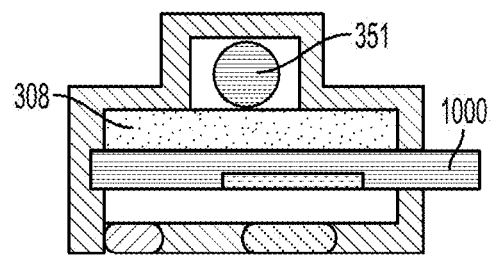
FIG. 4B
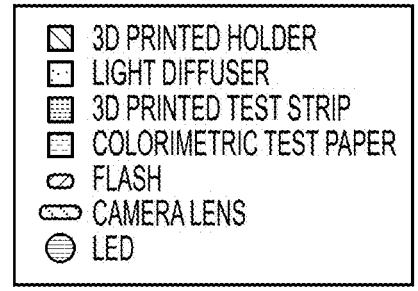
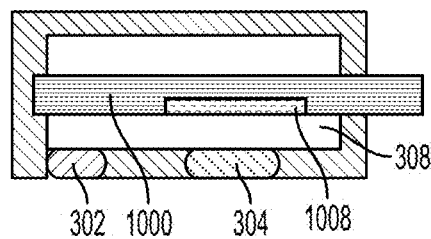
FIG. 4C

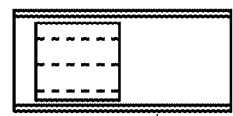
3D PRINTED SUPPORT
FIG. 9A
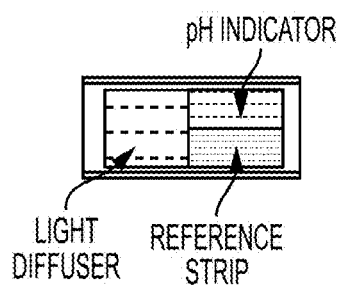
pH INDICATOR
LIGHT DIFFUSER    REFERENCE STRIP
FIG. 9B
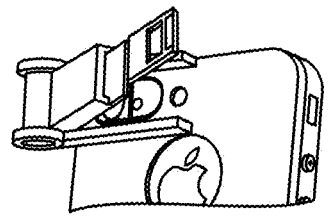
1. OPTICAL PART OPENED
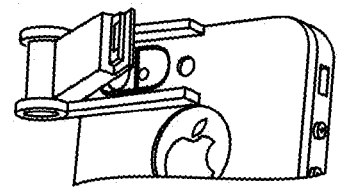
2. TEST STRIP INSERTED
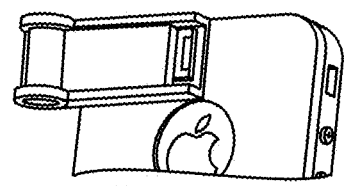
3. DATA ACQUISITION
FIG. 9C

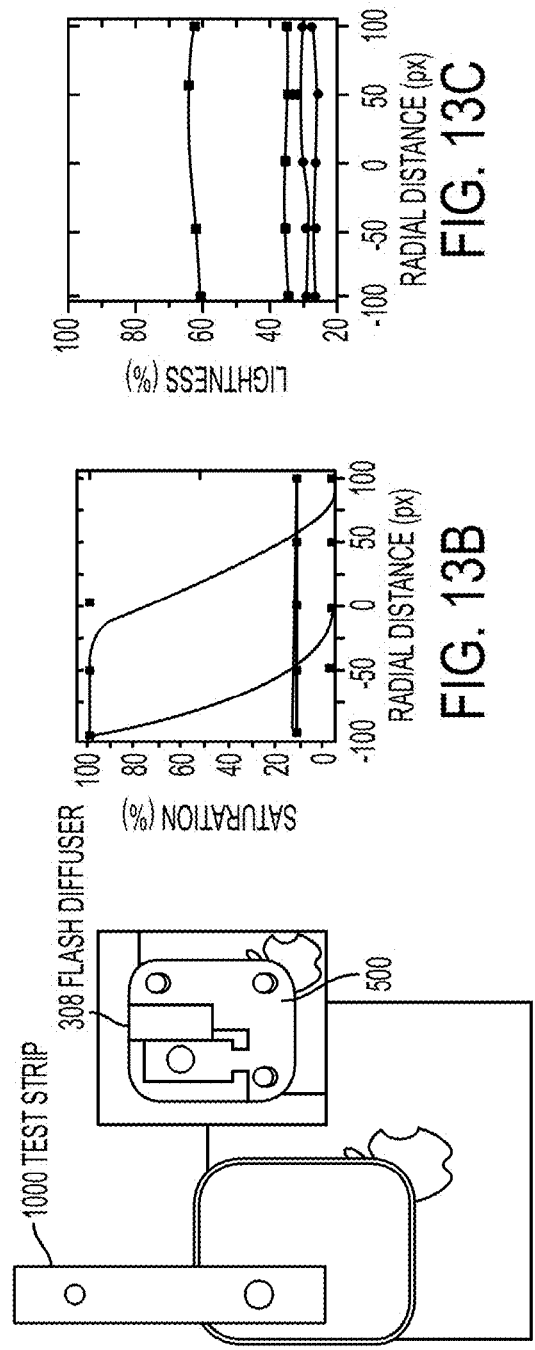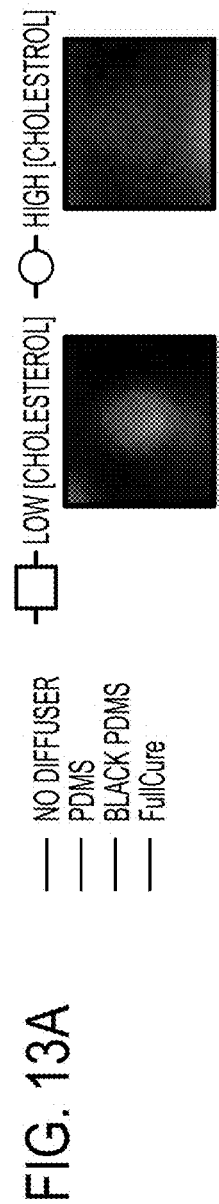

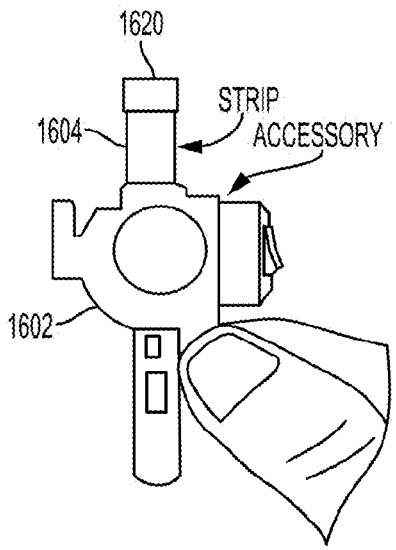
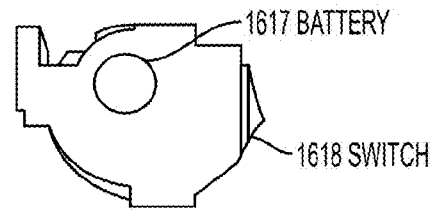
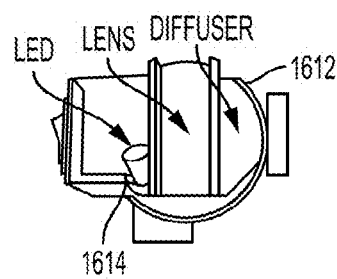
FIG. 16A  FIG. 16B  FIG. 16C
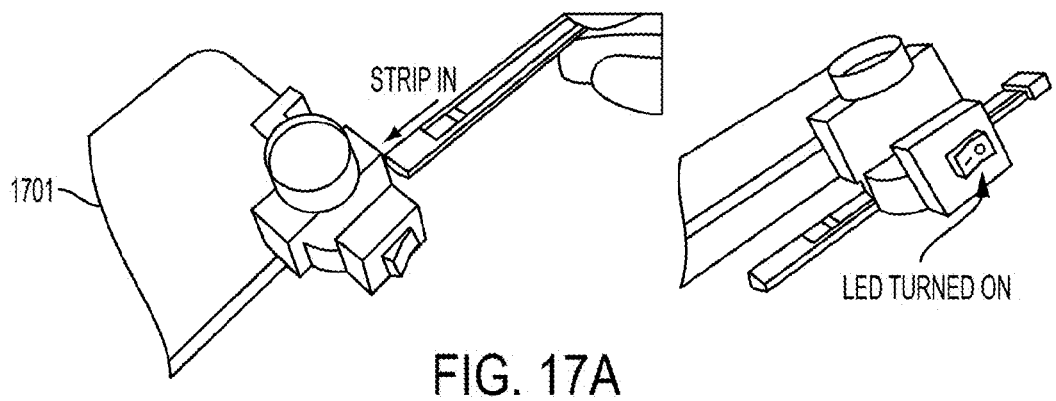
FIG. 17A
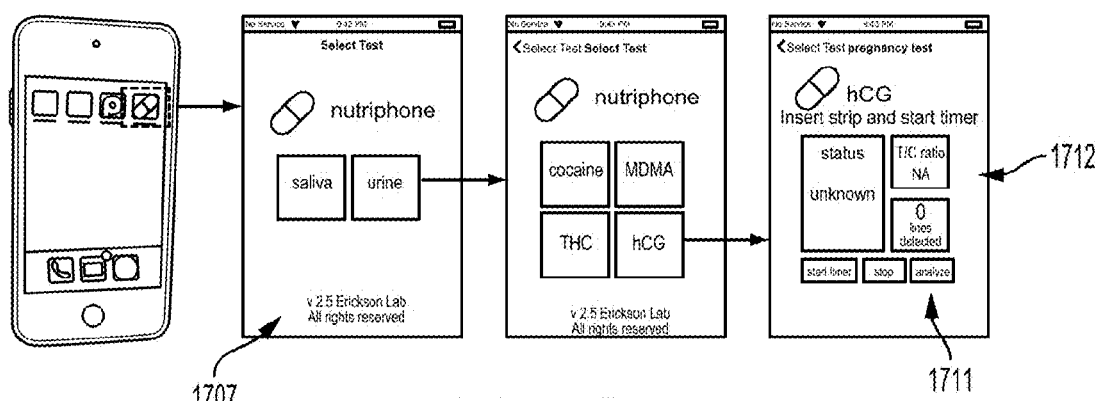
FIG. 17B

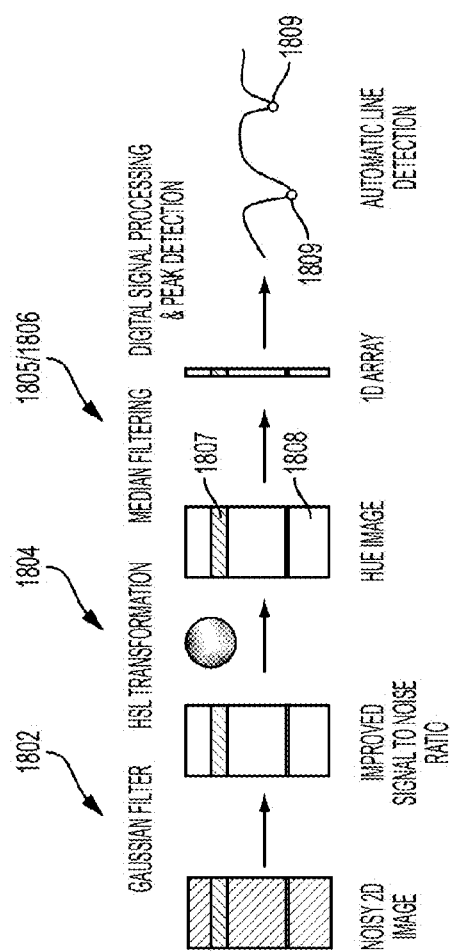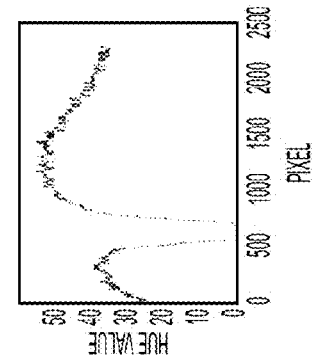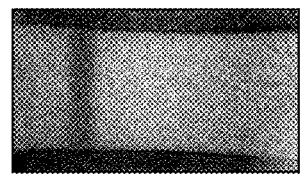
FIG. 18A
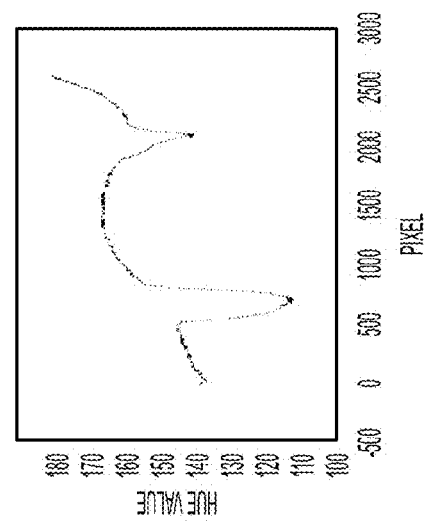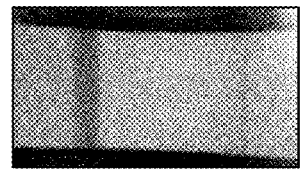
FIG. 18C
FIG. 18B

SMARTPHONE-BASED APPARATUS AND METHOD

RELATED APPLICATION DATA

The instant application is a U.S. bypass application under 35 USC 111(a) of International Application No. PCT/US14/12263 filed Jan. 21, 2014 and claims priority thereto, said PCT application claiming priority to U.S. provisional Application Ser. No. 61/754,733 filed Jan. 21, 2013, U.S. provisional Application Ser. No. 61/810,766 filed Apr. 11, 2013, U.S. provisional Application Ser. No. 61/892,154 filed Oct. 17, 2013, and U.S. Provisional Application Ser. No. 62/142,513 filed Apr. 3, 2015, the subject matter of all of which are incorporated by reference in their entireties.

GOVERNMENT FUNDING

The invention was made with funding from the US National Science Foundation under CAREER award #0846489. The U.S. government has certain rights in the invention.

TECHNICAL FIELD

Embodiments of the present invention relate generally to the field of biomolecular diagnostics and, more particularly to a smartphone-based, point-of-collection diagnostic system, methods, and components for obtaining consistent quantitative and/or qualitative measurements and analyses regardless of the smartphone platform in use.

BACKGROUND

Modern efforts in medicine and healthy living involve the delivery of personalized care and management to the patient. Due to the high variance inherent in biology, including in diagnostic criteria, treatment, and disease management, often the best solution for one patient is far from ideal for another. Before optimal treatment and healthy living for an individual can be prescribed by medical providers, the first step is collecting information about them; however, to date much of this data collection relies on questionnaires and surveys, diagnostic tests being prohibitively expensive, especially for groups that are not at immediate risk. These sorts of human input are often highly variable as they rely on a patient's ability to recall their past behavior as well as their integrity and embarrassment in admitting certain actions associated with (supposed) unhealthy living.

The cost and accessibility of traditional medical diagnostic instruments can and needs to be improved. Currently, diagnosis of disease can take days to weeks while results are sent off to a laboratory, and many diseases still cannot accurately be detected. Devices capable of quickly and accurately diagnosing multiple conditions could be applied to situations ranging from nutrition and vitamin management in first-world locales to antibiotic and vaccine triage in third-world villages. If created and packaged correctly, such devices could ease the burden on gateway physicians, provide impoverished countries with now inaccessible diagnostic capabilities, protect combatants from biological warfare agents, and increase health care access to the average person.

Lateral flow immunochromatographic assays have been widely adopted for diagnosing various diseases and medical conditions in point-of-care settings. These tests are rapid, simple and produce colorimetric signals that can be interpreted by untrained personnel. Unfortunately in most cases, the data interpretation of lateral flow tests depends on the end users who have to make judgments based on their observations, and therefore the results are largely susceptible to error. In recent years, there has been a desire to enhance the accuracy of the measurements, and/or to obtain quantitative information from the lateral flow tests. One exemplary case where higher accuracy is essential, and the subjectivity in determining the test outcome is inappropriate, is for the testing of controlled substances using the lateral flow tests.

The high demand for quantitative readouts has been reflected well by the increasing number of semi-portable readers on the market for analyzing the lateral flow assays. However the cost and size of these specialized reader systems still remain to be significant, and hamper their widespread adoption for many end consumers. Also, most of the commercial readers for lateral flow tests are only semi-portable and/or require connection to the computer systems to perform the required analysis. For example, the sizes of ESEQuant Lateral Flow Immunoassay Reader (Qiagen, Germany) and SkanMulti (Skannex, Norway) are still relatively bulky and thus are not truly portable. Furthermore, Skan-Multi functions only as an imaging system and requires a computer to analyze the acquired data.

One implementation of state-of-the-art diagnostics is as smartphone and/or tablet (i.e., portable computing) accessories where the computational power, read-out, data storage, and connectivity are provided by an existing device. The smartphone has penetrated nearly all aspects of our lives, affecting how we consume media including news and entertainment, how we track our finances and pay for goods and services, and how we monitor our health and fitness. However, for all of the benefits smartphones have provided, there is still little or no direct connection between smartphones and in vivo biochemistry. By enabling a direct link between a smartphone and small molecule detection, monitoring, and tracking, a number of new benefits could be realized in the fields of medicine and healthy living, including, e.g., simple diagnosis of disease and nutrient deficiencies; monitoring and tracking of existing conditions; and social media-enabled healthy living updates, competition, game playing, and mapping.

Moreover, some companies have indeed explored smartphone solutions for reading the lateral flow tests. For example, mReader software (MobileAssay, Colorado, USA) can be installed on smartphone systems and used to analyze the test strip images taken from the smartphone cameras. Although the use of smartphone systems to replace the specialized readers effectively addresses the aforementioned limitations, they do so at the expense of reliable imaging as the images are taken in the open environment whose lighting conditions cannot be accurately controlled.

Suboptimal nutrition is one of the most acute problems facing the developed and developing world today. Worldwide, there are more disability-adjusted life years lost to malnutrition than any other medical condition; it is reported that over 1,000,000 people die every year from vitamin A and zinc deficiencies, and 30% of all cancers are related to poor diet (by comparison genetics and obesity account for only 5% and 10% of all cancers respectively). Optimal pre-natal maternal folic acid levels are well co-related with a reduction in neural tube defects and evidence suggests that fetal brain development is enhanced by docosahexaenoic acid (DHA) intake. Micronutrient (i.e., vitamins and minerals) deficiencies have been tied to dozens of different health conditions including anemia, rickets, scurvy, cardiovascular disease, and cancer. Additionally, recent work has linked vitamin deficiencies to obesity, one of the major challenges facing the current generation.

The Copenhagen Consensus has identified tackling vitamin and micronutrient deficiencies as the most cost-effective intervention to further global development and progress in published reports since 2004. Domestically, the Institute of Medicine has concluded half of older adults in the United States who had hip fractures had serum levels of 25(OH)D less than 12 ng/mL; (25-hydroxyvitamin D [25(OH)D] is considered to be the best indicator of vitamin D; and, that levels below 20 ng/mL are inadequate for bone and overall health. The vast majority of vitamin and micronutrient analysis is done through blood collection via venipuncture, which is then sent away to a centralized laboratory. This analysis is slow, expensive, requires trained personnel, and is not widely available, particularly in resource-limited settings where micronutrient deficiency is most harmful. A combined HPLC-MS method is considered the industry standard for vitamin D testing, however ELISA kits and similar immunoassays are comparable in terms of sensitivity and accuracy, while being better suited for adaption to home use. Since micronutrient deficiencies are not often clinically obvious, these tests are typically done at the insistence of the patient. The fact that so many Americans are vitamin deficient testifies to the fact that the current methodologies are not working.

Salivary cortisol is a routinely used biomarker of stress and related psychological diseases. Commonly, cortisol is elevated in patients who experience a sudden stressor and returns to normal after a period of time whose length is dependent on the strength of the stressor. In patients with chronic stress disorders, such as PTSD, it has been difficult to co-relate absolute levels of cortisol at any given time with the diagnosis of a disorder due to the large number of confounders. A better approach would be to track cortisol, and other biomarkers, over time to look for trends that could be indicative of the onset psychological disease.

Every year hundreds of millions of people suffer from infectious diseases including respiratory infections, HIV/AIDS, diarrheal diseases, tuberculosis, and malaria. The agents that cause these diseases, including bacteria, viruses, fungi, etc., are often easily manageable with proper identification yet routinely go undetected because of the costs and difficulties associated with diagnostic technology. In some cases, such as tuberculosis, identifying the disease rapidly and on location can allow for preventative measures prohibiting the disease from spreading further. In other cases, such as HIV, keeping an acute-eye on antibody levels is critical in tracking the progress of the disease.

Kaposi's sarcoma (KS) is an opportunistic infectious cancer that first became widely known during the acquired immunodeficiency syndrome (AIDS) epidemic of the 1980s. During this time period, the appearance of symptoms of KS, red lesions on the skin, became signs that an individual was infected with human immunodeficiency virus (HIV) and KS itself became known as an AIDS-defining illness. As the battle against AIDS waged on, the introduction of highly active anti-retroviral therapy (HAART) helped reduce KS incidence. Years later, however, HIV infected individuals still contract KS at a higher occurrence than when compared to the pre-AIDS era. Today, KS is the fourth leading cancer in sub-Saharan Africa, and in some countries, such as Uganda, is the most prevalent cancer in men. The root cause of KS is Human herpes virus 8 (HHV-8), more commonly referred to as Kaposi's sarcoma associated herpes virus (KSHV). While the virus is often asymptomatic in healthy individuals, a number of populations, including those immune-compromised by HIV, are vulnerable to its symptoms. The virus is commonly believed to be transmitted through saliva and in some regions rapidly spreads, beginning in childhood affecting large portions of the population, reaching seroprevalence of over 50%. Like other herpes viruses, KSHV can establish a latent infection and remains without causing any disease for the remaining life in most infected hosts, being necessary but not sufficient of KS development.

In the developed world, medical professionals diagnose KS with sufficient accuracy. If typical hematoxylin and eosin (H&E) staining are applied to a KS biopsy section a number of unique features can be observed, including many and large vascular spaces as well as high numbers of spindle cells thought to be of lymphatic endothelial origin. However, due to the existence of similarly presenting diseases, such as bacillary angiomatosis (BA), identification of these features is not sufficient for diagnosis of KS. In modern hospitals this is solved through immunohistochemistry staining for protein markers of KSHV, or through application of PCR for KSHV sequences. However, neither of these techniques is readily adaptable for use in the developing world where KS is most prevalent.

The alarming increase in premature deaths due to heart disease in the developed world has resulted in numerous efforts to make blood cholesterol measurements accessible outside the clinical setting. It is estimated that 60% of adults in the US have high cholesterol (over 200 mg/dl), with 37 million among them having very high cholesterol (over 250 mg/dl). Long-term studies on the effect of serum cholesterol on coronary heart disease mortality indicate that there is a 17% increase in mortality rate for every 20 mg/dl increase in serum cholesterol levels above 210 mg/dl. Monitoring cholesterol levels is important because it can empower people to make lifestyle choices for preventing heart disease later in life. For some people, improving diet and increasing exercise can lower overall cholesterol, but in some cases medication needs to be prescribed. Products such as Cardiochek and Cholestech have been on the market for over a decade; however home cholesterol testing is still not common. A recent study suggested that current cholesterol kit users are interested in easier ways of tracking results and that they would test more frequently if supplies were more affordable. The accuracy of those devices is also a major user concern and has been addressed in several publications.

Finding a solution to the aforementioned challenges and problems directly motivated the development of lab-on-a-chip based point-of-care diagnostics beginning some 15 years ago. The technical vision behind these kinds of systems comprised two parts: a consumable "chip" that contained microfluidics and a biosensor, and a "reader" instrument that interpreted the signal from the chip and provided results to the operator. Since this vision was first put forward, the technology has advanced at an incredible rate to the point where we now have devices that can operate over a million microfluidic valves in parallel, portable PCR machines for pathogen detection, nanosensors that can detect a handful of molecules, and numerous other systems. These developments have significantly reduced the size of the sample required to perform a blood analysis.

Smartphones have the potential of addressing all these issues by eliminating the need for separate test kits. Test strips could be imaged directly on a smartphone and the processed data can be stored for tracking or sent via e-mail directly to a physician. Smartphone accessories for the detection of biomarkers in bodily fluids have been the subject of extensive investigation because they have the potential of greatly decreasing the cost and increasing the availability of heath care in the world.

It is predicted that by 2016 there will be 250 million smartphones in use in the US. A good portion of the complexity required to make and interpret a quantitative in-vitro measurement is already embedded in smartphones, resulting in a paradigm shift in the "razor and blades" model. Put simply, most consumers now already own the expensive part, the "Razor," in the form of a smartphone; all one needs then is the blades.

The inventors have recognized that quantitative analyses of bodily fluids like sweat, saliva, urine, blood, and others would provide a deep wealth of physiological information. The inventors have also recognized that, in addition to mobile, point-of-collection devices and methods that address the challenges outlined above, there is an intense need for the ability to obtain accurate, consistent, and standardized quantitative measurements and, independent of the smartphone platform being used, the benefits and advantages of which would contribute to better quality of life.

These and other objects, benefits, and advantages provided by the solutions enabled by the embodied invention will be described in detail below with reference to the accompanying figures and as set forth in the appended claims.

SUMMARY

Embodiments of the invention are methods and systems (and components thereof) for obtaining and presenting (i.e., displaying or communicating out) quantitative, colorimetric-based measurements of target analytes as well as enabling accurate reading and analyses of lateral flow assays using a smartphone platform that is accurate, consistent and reliable independent of the smartphone platform being used.

Definitions

As used herein, the term 'smartphone,' 'smartphone platform,' or 'smartphone-type device/system' (hereinafter "smartphone") means a mobile apparatus that is capable of running a programmed application suitable for executing the embodied functionality. While suitable traditional smartphones may include products such as, e.g., the iPhone, iPad (Apple, Inc.), Android-based devices, and other well known devices and associated operating systems, the term smartphone as discussed and embodied herein is intended to include any digital mobile device such as smartphones, tablets, phablets, smart watches, and other current or future 'smartphone' platforms having similar minimal functionality. In this regard and for the sake of clarity, a 'laptop' computer would not necessarily be covered under the definitional use of the term 'smartphone;' nor would a computing device that could be made 'portable' or 'mobile' by an accompanying apparatus that might give it portability or mobility. Thus, the term 'smartphone' will be used herein (including the claims) to mean devices as discussed within the paragraph above.

The term 'modular test platform' as may be used herein (and in the claims) means a reusable or disposable medium capable of receiving a target sample and having the appropriate chemistry and form factor to be used in the embodied smartphone and enable the embodied colorimetric reaction. Practical examples of embodied modular test platforms include, but are not limited to, various custom or commercially available 'test strips.'

The term 'rear surface' as may be used herein (and in the claims) in conjunction with 'test strip' means the surface of the test strip facing away from the smartphone camera in an operational mode of the system.

The term 'colorimetric test,' 'colorimetric assay,' or 'colorimetric reactive test platform' as may be used herein (and in the claims) means at least a measurable color change from one color to a different color or a measurable change in intensity of a particular color, in the presence of the analyte.

The term 'rapid' as may be used herein (and in the claims) means 'essentially in real time' (e.g., seconds, minutes).

The term 'point-of-collection' as may be used herein (and in the claims) means making a rapid target measurement at the time a sample is collected on a modular diagnostic test platform (e.g., test strip) in possession of the user and then inserted into the embodied smartphone system, not at a later time, for example, after a sample has been collected and sent to a laboratory.

The term 'suitable' as may be used herein (and in the claims) means having the qualities that are correct, needed, or appropriate for something, especially as a person skilled in the art would understand.

The term 'about' as may be used herein (and in the claims) means the amount of the specified quantity plus/minus a fractional amount thereof that a person skilled in the art would recognize as typical and reasonable for that particular quantity or measurement.

The term 'substantially' as may be used herein (and in the claims) means as close to or similar to the specified term being modified as a person skilled in the art would recognize as typical and reasonable; for e.g., within typical manufacturing and/or assembly tolerances, as opposed to being intentionally different by design and implementation.

An embodiment of the invention is a method for obtaining a point-of-collection, selected quantitative indicia of an analyte on a test platform with a smartphone. Illustrative method steps include providing a modular, colorimetric reactive test platform having a test region and a calibration region; providing an analyte to be tested on the test region of the modular, colorimetric test platform, wherein the test region is adapted to enable a colorimetric reaction to the analyte; obtaining a color image of the test region containing the analyte and the calibration region; selecting an array of pixels in each of the color images of the test region containing the analyte and the calibration region; determining a median RGBA color value for each of the arrays of pixels; converting the median RGBA color value for each of the arrays of pixels to a respective Hue-Saturation-Luminosity (HSL or HSV) test color space value and a HSL or HSV calibration color space value; providing a calibration indicia that relates a selected quantitative indicia of the analyte to a characteristic of the HSL or HSV calibration color space value; and associating a median HSL or HSV test color space value with the HSL or HSV calibration color space value to determine the selected quantitative indicia of the analyte. The embodied method may further be characterized by the following illustrative, exemplary, non-limiting aspects, features, or steps:

wherein the colorimetric reactive test platform is sensitive to at least one of a chemical colorimetric reaction, an enzymatic colorimetric reaction, and a gold nanoparticle colorimetric reaction;

wherein the modular, colorimetric test platform is a disposable test strip;

wherein the indicia of the analyte is one of pH, cholesterol, and vitamin D;

wherein the calibration region maintains a constant color in the presence of a varying amount of the selected indicia of the analyte;

wherein the calibration region includes a plurality of calibration regions each of which has a different calibration color;

wherein the calibration indicia is a calibration curve that relates the selected quantitative indicia of the analyte to a hue value of the HSL or HSV calibration color space value;

obtaining the color image of the test region containing the analyte and the calibration region using a smartphone including a light source and an image detector;

displaying the determined selected quantitative indicia of the analyte on the smartphone;

providing a smartphone accessory that can be removeably coupled to the smartphone, wherein the smartphone accessory is adapted to receive the modular, colorimetric test platform, further wherein at least one of the modular, colorimetric test platform and the smartphone accessory includes a light diffuser and/or a light-diffusing pathway so as to ensure a uniform and repeatable illumination of at least a desired region of the modular, colorimetric test platform, further wherein the smartphone accessory is substantially light-tight when the test platform is disposed therein, so as to enable consistent internal illumination conditions independently of any external conditions;

wherein obtaining a color image of the test region containing the analyte and the calibration region further comprises illuminating a rear surface of the test strip that is facing the light source with diffused light from the light source wherein the light source is one of an internal smartphone flash source and an external LED source;

time stamping the determined selected quantitative indicia of the analyte and storing the determined value for future access;

location stamping the determined selected quantitative indicia of the analyte and storing the determined value for future access;

storing the time and/or location data in at least one of a readable file in the smartphone, an external readable file, and in a Cloud file;

determining a temporal and/or a location trend of a plurality of the determined selected quantitative indicia of the analyte;

correlating the determined selected quantitative indicia of the analyte to a related selected metric and displaying a value of the related selected metric on the smartphone;

wherein the analyte is one of sweat, saliva, blood, tears, urine, and other bodily fluids;

wherein the step of obtaining a color image of the test region containing the analyte and the calibration region comprises illuminating a rear surface of the modular, colorimetric test platform.

An embodiment of the invention is a method for obtaining a point-of-collection, selected qualitative and/or quantitative indicia of an analyte on a test platform. In an exemplary aspect, the method involves providing a modular assay test platform (e.g., test strip) having at least one test region and a control region; providing an analyte to be tested on the at least one test region; obtaining an image of the at least one test region containing the analyte and the control region;

selecting an array of pixels in the image of the at least one test region containing the analyte and the control region; determining a RGBA color value for each of the arrays of pixels; extracting a test image region for analysis; converting the RGBA array to an alternate color space as determined by the specific test including but not limited to HSL, HSV, or greyscale; determining one of a median, mean, maximum, minimum, or other statistical measure of the color or intensity value for various regions of the test platform that may or may not contain test or control areas and creating at least a 1D array containing these values; if necessary, determining a low-frequency variation in color or intensity value over the array and, if necessary, performing illumination correction and background subtraction; detecting a peak or valley in the adjusted array corresponding to the test and control regions to be measured; determining a depth, width, height (for example, based on intensity or color maxima/minima), and/or area (for example, based on integrated color or intensity)) FIG. 19) of these peaks or valleys which correspond to detection or control regions of the test platform; and determining a qualitative presence of the selected indicia of the analyte by the number of peaks or valleys present, and/or a quantitative value of the selected indicia of the analyte by quantitative comparison of two or more peaks or valleys. The embodied method may further be characterized by the following illustrative, exemplary, non-limiting aspects, features, or steps:

wherein the assay test platform is sensitive to at least one of a chemical colorimetric reaction, an enzymatic colorimetric reaction, and a gold nanoparticle colorimetric reaction, including a lateral flow type immunoassay;

wherein the assay test platform is a disposable lateral flow immunochromatographic test strip;

obtaining the image of the at least one test region containing the analyte and the control region using a smartphone including a light source and an image detector;

comprising using a brand-independent or operating-system-independent smartphone;

further comprising displaying the determined selected indicia of the analyte on the smartphone;

further comprising at least one of time stamping and location stamping the determined selected quantitative indicia of the analyte and storing the determined value for future access;

comprising storing the time and/or location data in at least one of a readable file in the smartphone, an external readable file, and in a Cloud file;

further comprising determining a temporal and/or a location trend of a plurality of the determined selected quantitative indicia of the analyte;

further comprising correlating the determined selected quantitative indicia of the analyte to a related selected metric and displaying a value of the related selected metric on the smartphone;

further comprising providing a smartphone accessory that includes:

a housing that can be removeably attached to the smartphone in a manner that at least optically couples the smartphone accessory to a resident smartphone camera;

a lens that allows for adjustment of the focal length of the smartphone camera to enable imaging of the test platform in a compact device, wherein the housing is opaque such that the smartphone accessory is substantially externally light-tight when the test platform is disposed therein, further wherein the housing includes at least one of a designed-in optical pathway and a light diffuser in the housing for providing diffuse illumination of a surface of the test platform disposed therein from an internal light source resident in the housing or an external light source resident in the smartphone to which the smartphone accessory can be attached;

wherein the light source is one of an internal smartphone flash source and an external LED source;

wherein obtaining the image of the test region or regions containing the analyte and the control region or regions further comprises illuminating a surface of the test platform that is illuminated by the light source with diffused light from the light source;

wherein the analyte is one of sweat, saliva, blood, tears, urine, and other bodily fluids;

wherein the step of obtaining the image of the test region or regions containing the analyte and the control region or regions comprises illuminating a surface of the modular, colorimetric test platform;

wherein obtaining an image of the at least one test region comprises obtaining multiple images denoting changes in the indicia over time, which can be used to provide an improved estimate of the initial concentration of the analyte;

wherein obtaining an image of the at least one test region comprises obtaining multiple images denoting changes in the indicia over time, which can be used to serve as a method for detecting an error with the test.

An embodiment of the invention is a smartphone accessory for use in a smartphone-based point-of-collection, colorimetric-based, quantitative measuring system. The smartphone accessory includes a housing that can be removeably attached to the smartphone in a manner that at least optically couples the smartphone accessory to a resident smartphone camera, wherein the housing is opaque such that the smartphone accessory is substantially externally light-tight when a test strip is disposed therein, further wherein the housing includes at least one of a designed-in optical pathway and a light diffuser in the housing for providing diffuse illumination of a surface of the test strip disposed therein from an internal light source resident in the housing or an external light source resident in the smartphone to which the smartphone accessory can be attached. The embodied smartphone accessory may further be characterized by the following illustrative, exemplary, non-limiting aspects, features, or limitations:

wherein the designed-in optical pathway in the housing comprises a wall that creates an indirect optical path between the external light source resident in the smartphone to which the smartphone accessory can be attached and a resident smartphone camera in the smartphone to which the smartphone accessory can be attached;

wherein the light diffuser is disposed intermediate the external light source resident in the smartphone to which the smartphone accessory can be attached and a non-colorimetric-reactive region of the test strip when the test strip is disposed in the housing;

wherein the at least one of the designed-in optical pathway and the light diffuser is disposed in a manner to provide diffuse illumination of a rear surface of the test strip;

further comprising a light source disposed in the housing; a light diffuser disposed intermediate the light source and a resident smartphone camera in the smartphone to which the smartphone accessory can be attached, in a manner to provide diffuse illumination of a rear surface of a test strip when the test strip is disposed in the housing; and a power source for the light source, disposed in the housing.

An embodiment of the invention is a smartphone accessory for use in a smartphone-based point-of-collection, system. In an exemplary aspect, the system includes a housing that can be removeably attached to the smartphone in a manner that at least optically couples the smartphone accessory to a resident smartphone camera; a lens that allows for adjustment of the focal length of the smartphone camera to enable imaging of the test strip in a compact device, wherein the housing is opaque such that the smartphone accessory is substantially externally light-tight when a test strip is disposed therein, further wherein the housing includes at least one of a designed-in optical pathway and a light diffuser in the housing for providing diffuse illumination of a surface of the test strip disposed therein from an internal light source resident in the housing or an external light source resident in the smartphone to which the smartphone accessory can be attached. The embodied smartphone accessory may further be characterized by the following illustrative, exemplary, non-limiting aspects, features, or limitations:

wherein the designed-in optical pathway in the housing comprises a wall that creates an indirect optical path between the external light source resident in the smartphone to which the smartphone accessory can be attached and a resident smartphone camera in the smartphone to which the smartphone accessory can be attached;

wherein the light diffuser is disposed intermediate the external light source resident in the smartphone to which the smartphone accessory can be attached and a non-colorimetric-reactive region of the test strip when the test strip is disposed in the housing;

wherein the at least one of the designed-in optical pathway and the light diffuser is disposed in a manner to provide diffuse illumination of a surface of the test strip;

further comprising:
a light source disposed in the housing;
a light diffuser disposed intermediate the light source and a resident smartphone camera in the smartphone to which the smartphone accessory can be attached, in a manner to provide diffuse illumination of a surface of a test strip when the test strip is disposed in the housing; and
a power source for the light source, disposed in the housing.

An embodiment of the invention is a portable, modular, point-of-collection, colorimetric-based diagnostic system. Illustrative limitations include a smartphone including a light source and an image detector; a smartphone accessory that can be removeably coupled to the smartphone, wherein the smartphone accessory is adapted to receive a modular, colorimetric test strip in a manner that exposes a surface of the test strip to a light output from the light source, further wherein the smartphone accessory is substantially light-tight when the test strip is disposed therein so as to enable consistent internal illumination conditions independently of any external conditions; and an executable application resident in the smartphone that, in operation, performs the following steps: acquires an image of at least a portion of the test strip; stores the image as an RGBA byte array; splits the image into a test image and a calibration image; for the calibration image: extracts a calibration array of pixels; determines a median RGBA color value for the calibration array of pixels; converts the median RGBA color value for the calibration array of pixels to a calibration Hue-Saturation-Luminosity (HSL or HSV) color space value; adjusts the calibration HSL or HSV color space value to a calibration indicia of a selected quantitative indicia of an analyte to be measured; and for the test image: extracts a test array of pixels; determines a median RGBA color value for the test array of pixels; associates the median RGBA color value for the test array of pixels to the calibration HSL or HSV color space value; and determines a quantitative value of the selected indicia of the analyte to be measured. The embodied system may further be characterized by the following illustrative, exemplary, non-limiting aspects, features, or limitations:

wherein the light source is an internal flash source of the smartphone;

wherein the light source is an LED disposed in the smartphone accessory, further comprising a battery in the smartphone accessory to power the LED;

wherein the system is smartphone platform-independent;

wherein the smartphone accessory is an unpowered component;

wherein the smartphone accessory includes a light diffuser and/or a light-diffusing pathway so as to ensure a uniform and repeatable illumination of at least a desired region of the modular, colorimetric test platform and which provides a uniform, diffuse light exposure from the light source to a rear surface of the test strip;

a colorimetric reactive test strip that is removeably disposable in the smartphone accessory;

wherein the colorimetric reactive test strip includes a colorimetric reactive test region and a non-colorimetric reactive calibration region;

wherein the colorimetric reactive test region is at least one of chemically colorimetric reactive, enzymatically colorimetric reaction, and gold nanoparticle colorimetrically reactive;

wherein the colorimetric reactive test strip includes a light diffuser;

wherein the light diffuser is one of a PDMS membrane and an adhesive tape disposed on at least a portion of a surface of the test strip;

wherein the light diffuser is disposed on the at least a portion of a surface of the test strip is such a manner to provide diffuse illumination to a rear surface of the test strip;

wherein the non-colorimetric reactive calibration region comprises a glossy material.

An embodiment of the invention is a portable, modular, point-of-collection, colorimetric-based diagnostic system. In an exemplary aspect, the system includes a smartphone including an image detector; a smartphone accessory as described herein above; and an executable application resident in the smartphone that, in operation, performs the following steps: obtaining an image of the at least one test region containing the analyte and the control region; selecting an array of pixels in the image of the at least one test region containing the analyte and the control region; determining a RGBA color value for each of the arrays of pixels; extracting a test image region for analysis; converting the RGBA array to an alternate color space as determined by the specific test including but not limited to HSL, HSV, or greyscale; determining a median color or intensity value for the pixels in each row, and creating at least a 1D array containing these values; determining a low-frequency variation in color value over the array and performing illumination correction and background subtraction; detecting a peaks or valley in the adjusted array corresponding to the test and control lines to be measured; determining a depth or height (intensity maxima/minima) and/or area (integrated intensity) (FIG. 19) of these peaks which correspond to detection lines of the test strip; and determining a qualitative presence of the selected indicia of the analyte by the number of peaks present, and/or a quantitative value of the selected indicia of the analyte by quantitative comparison of two or more peaks. The embodied system may further be characterized by the following illustrative, exemplary, non-limiting aspects, features, or limitations:

wherein the light source is an internal flash source of the smartphone;

wherein the light source is an LED disposed in the smartphone accessory, further comprising a battery in the smartphone accessory to power the LED;

wherein the system is smartphone platform-independent;

wherein the smartphone accessory is an unpowered component;

further comprising a colorimetric reactive test strip that is removeably disposable in the smartphone accessory;

wherein the colorimetric reactive test strip includes at least one test region and a control region;

wherein the colorimetric reactive test region is at least one of chemically colorimetric reactive, enzymatically colorimetric reaction, and gold nanoparticle colorimetrically reactive, including a lateral flow type immunoassay;

wherein the light diffuser is disposed on the at least a portion of a surface of the test strip is such a manner to provide diffuse illumination to a surface of the test strip.

Additional features and advantages of the invention will be set forth in the detailed description to follow, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

BRIEF DESCRIPTION OF THE DRAWINGS

The present invention will be more fully understood and appreciated by reading the following Detailed Description in conjunction with the accompanying drawings, in which:

FIG. 3A shows an overview of a modular smartphone 'app' and its operation, in which the user selects the desired test strip from a menu of pre-calibrated test options; FIG. 3B the app automates the process of image acquisition and processing for the desired application. The top image shows a sweat pH and electrolyte interface and the bottom image shows a salivary monitoring interface; FIG. 3C a plot of the data is produced to demonstrate trends over time, according to an illustrative embodiment of the invention;

FIG. 4A schematically shows three designs for creating uniform lighting within a smartphone accessory holder: a wall is provided to create an indirect optical path from the flash to the test strip and the camera; FIG. 4B a LED is placed within the cavity behind a diffuser to generate low-power, uniform light to illuminate a rear surface of a test strip; FIG. 4C is an optically diffusive material is placed in front of the camera flash to spread the light from the flash uniformly around the accessory cavity to illuminate a rear surface of a test strip, according to illustrative aspects of the invention;

FIG. 9A and FIG. 9B, respectively, show a 3D printed black polymer test strip support and a test strip containing a pH indicator region, a reference region, and a light diffusive material. FIG. 9C shows a smartphone accessory; all according to an illustrative aspect of the invention;

FIG. 13A shows a picture of a smartphone accessory and the test strip used; the inset shows the inside of the accessory with a black PDMS diffuser; FIG. 13B shows a variation in saturation across a 200 px area in the center of a low cholesterol (<100 mg/dl) test strip for different diffusers in the accessory; FIG. 13C shows variation in lightness across a 200 px area between the low cholesterol strip (<100 mg/dl) and high cholesterol (>400 mg/dl) strip for two different diffusers. FIG. 13D shows typical smartphone acquired images of the colorimetric reaction, at low (<100 ma/dl) and high (>400 mg/dl) cholesterol concentrations, according to an illustrative aspect of the invention;

FIG. 16A shows a smartphone accessory assembled; FIG. 16B shows a front side showing the battery placement; FIG. 16C shows a back side showing the LED, lens, switch and diffusor incorporation, according to an exemplary aspect of the invention for qualitative and/or quantitative readout of lateral flow immunochromatographic assays, and associated methods and applications;

FIG. 17A illustrates operation of the smartphone based system for qualitative and/or quantitative readout of lateral flow immunochromatographic assays: hardware; FIG. 17B software;

FIG. 18A schematic of the image processing algorithm. The raw image is first filtered to reduce the signal-to-noise ratio, then transformed to HSL so the hue can be used for line detection. The image is then reduced to one dimension with a row-wise median filter, and the local minima are detected in the 1D signal. The shape and height of the found peaks can also be analyzed to give a quantitative comparison of the test and control lines; FIG. 18B positive test result—the raw image of the test strip taken with the device and the processed data with two detected minima; FIG. 18C negative test result—the raw image of the test strip taken with the device and the processed data with one detected minimum, according to an illustrative embodiment of the invention.

DETAILED DESCRIPTION OF NON-LIMITING, EXEMPLARY EMBODIMENTS OF THE INVENTION

Figure 1:
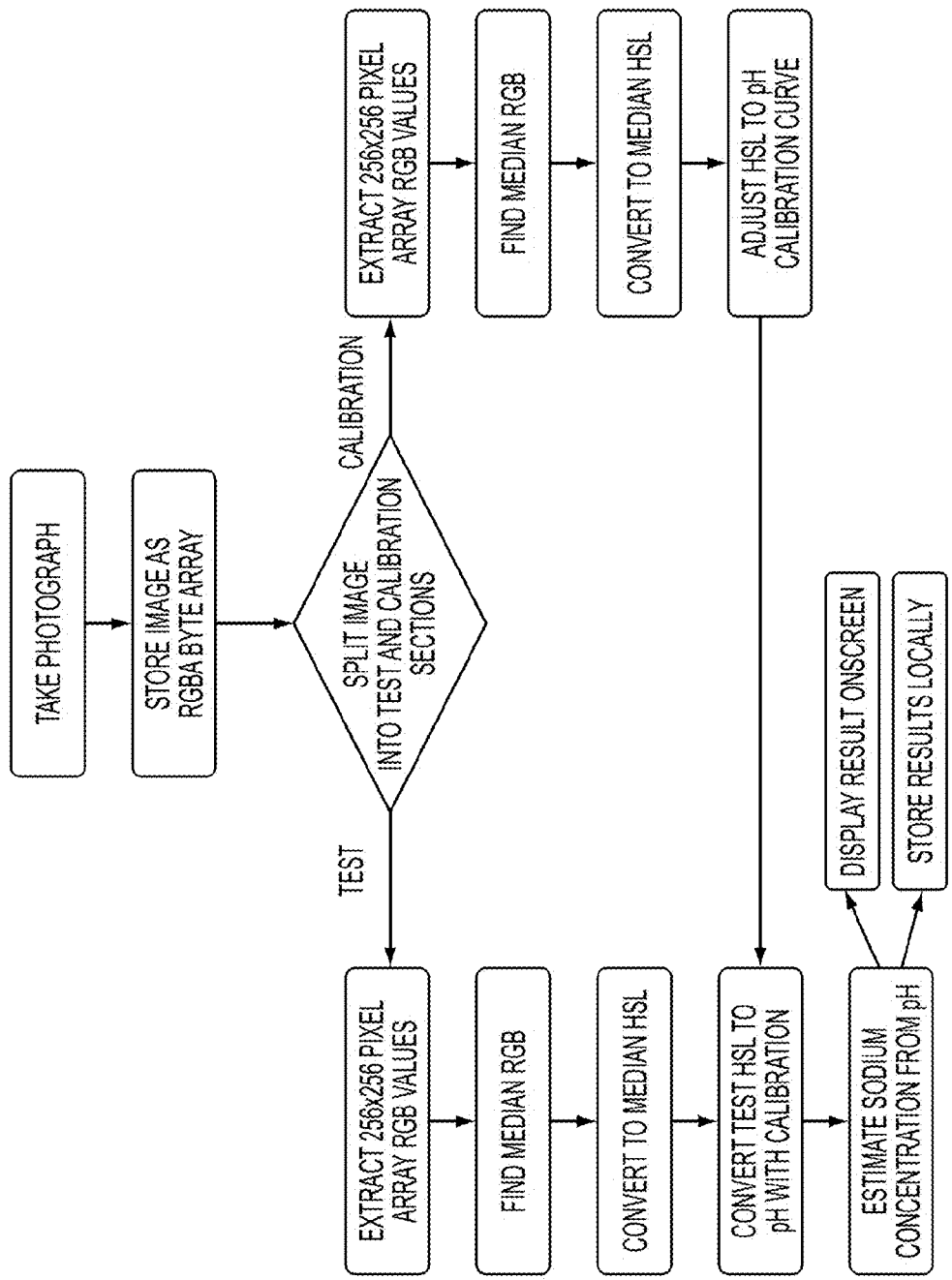
FIG. 1 illustrates the steps of a method for obtaining a point-of-collection, selected quantitative indicia of an analyte on a test platform, according to an embodiment of the invention.

Embodiments of the invention are methods, apparatus, and systems pertaining to obtaining and presenting (i.e., displaying or communicating out) quantitative, colorimetric-based measurements of target analytes using a smartphone platform that are accurate, consistent and reliable independent of the smartphone platform being used. The achievement of accurate, consistent and reliable quantitative measurements of target analytes is possible with the use of commercially available test strips on which a deposited target sample (e.g., saliva, sweat, blood, urine, others) can undergo a colorimetric reaction (e.g., chemical colorimetric reaction, enzymatic colorimetric reaction, nanoparticle colorimetric reaction) initiated by diffuse illumination of the test strip, image recording by the smartphone camera, and image processing within the smartphone by a resident software application ('app'). More particularly, the embodied invention includes a removable (or detachable from a smartphone) smartphone accessory into which the test strip is disposed. The smartphone accessory provides an internal environment that is light-tight such that essentially all light not used for imaging the test strip and colorimetric reaction is excluded regardless of ambient conditions, as well as an illumination modality in the form of a designed-in optical pathway or a light diffuser that insures a consistent optical and imaging environment for every test strip, thus rendering the embodied system and method smartphone-platform-independent.

Exemplary embodiments of a smartphone-based method, a smartphone system, a smartphone app, a smartphone accessory and, where relevant, a test strip, are described in detail herein below. While the disclosure describes examples of target analytes of vitamin D, sweat, saliva, pH and cholesterol, other analytes as listed in Table 1, and others not listed but understood by those skilled in the art, may likewise be similarly measured.

The colorimetric test strips utilized in conjunction with the embodied invention are not necessarily part of the invention per se, although they play a significant role in the operability and enablement of the embodied invention. In this regard, the colorimetric-reactive test region on the test strips disclosed herein are for the most part commercially available and may already appear on test strips that may also include a calibration or reference (non-colorimetric-reactive) region on a (typically front) surface thereof. The test region of the test strips contains the appropriate chemistry to enable a colorimetric reaction that may include a chemical colorimetric reaction, an enzymatic colorimetric reaction, or a (e.g., gold) nanoparticle colorimetric reaction.

Various exemplary test strips suitable for use in conjunction with the embodied invention are illustrated in FIGS. 6, 7, 9b, 11 and 12. Examples of the embodied invention will now be described in conjunction with these various test strip modalities.

FIG. 9(b) shows an early proof of concept test strip that contains a pH indicator (test) region for measuring a sweat sample, a reference region, and a light diffusive material, as shown. This test strips is shown assembled on a 3D printed black polymer support in FIG. 9(a) for use in a smartphone accessory (holder) as illustrated in FIG. 9(c). The dimensions of this test strip are about 1 cm×2 cm and were designed to fit the illustrated holder. The test strip and holder were optimized for data acquisition with the camera of an iPhone 4. The pH indicator paper strip was chosen to cover the physiological range of pH values (pH 5 to pH 8). The pH paper was cut in 0.5 cm by 1 cm strips and inserted in the holder through the side. The reference paper strip was chosen to aid in the calibration of the measurements and was a green glossy reference paper. Green falls within the range of color variation for the pH paper, while the glossy nature of the paper ensured that the color of the reference did not change when the strip comes in contact with sweat. The light diffusive materials that were used were PDMS and adhesive tape. Adhesive tape offered a simple fabrication procedure and robustness of the assembled test strip. In the system illustrated in FIG. 9(c), the resident flash of the cell phone camera was used to illuminate the test strip. The light diffuser was incorporated between the flash and the test strip in order to distribute the light from the flash evenly across the surface of the test strip. The test strip shown in FIG. 9(b) redirected light from the flash to diffusely illuminate the rear surface of the test strip.

In this example, sweat was collected from the forehead of a user after exercising for 5 to 10 minutes. The test strip was used to directly wipe the sweat off the forehead with the pH indicator paper in direct contact with the sweat for about five seconds to ensure that the pH indicator paper was fully and uniformly soaked with sweat. Once the sweat was collected, the user opens the optical holder and introduces the test strip with the pH indicator paper facing the smartphone camera as shown in FIG. 9(c). After closing the optical holder such that there is no external light reaching the test strip, the user waited about one minute before taking the measurement to allow the pH indicator paper to reach a uniform and stable color. The user then takes a photo-image using the smartphone's camera and a resident smartphone application is used to obtain quantitative pH and sodium concentration values.

The smartphone software application was used to both image the colorimetric test strip and determine the pH of the sample. Upon opening the application, the user is prompted to place the used test strip into the strip holder accessory behind the camera. After loading the strip, the user presses a "Camera" button, and the smartphone camera takes a photograph of the strip for image processing. When the user runs the "Analysis" function, the application then stores the photograph into an RGBA byte array so that the red, blue, green, and alpha (transparency) values for each pixel can be accessed independently. The alpha channel can be discarded as it does not vary with analyte concentration.

The camera image is split into sections, with one section containing the sample to be measured and additional sections for each of the (one or more) calibration colors, and a 256×256 array of pixels is selected in each section for analysis. The median color of each of these 256×256 pixel segments can then be determined separately. Looping through the byte array, the red, green, blue, and alpha values are extracted and stored for each pixel in a given region, and then stored in additional arrays. These arrays are then sorted in ascending order and the median value is selected for each color channel. The median value is used instead of an averaging function because of the nature of RGBA values; a small number of white pixels (with R, G, and B values of 255) would have a minimal impact on a median color value, but could greatly distort the mean.

Figure 10A:
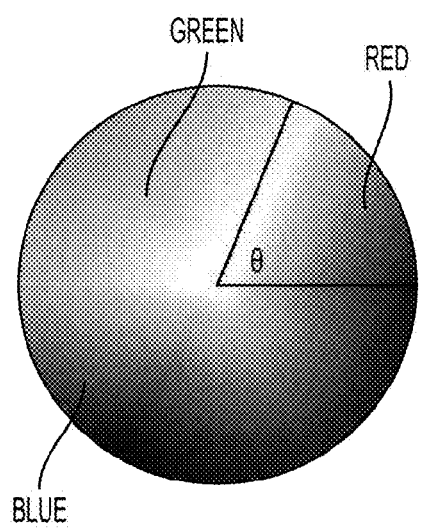
FIG. 10A illustrates the merits of the HSV color space: The hue value gives the color as an angle transitioning from red through blue (counterclockwise)
Figure 10B:
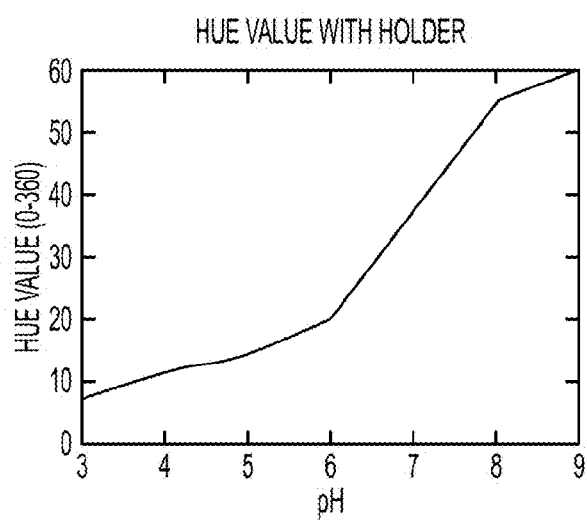
FIG. 10B The hue increases monotonically with increasing pH and is linear over a large pH range; according to an illustrative aspect of the invention.
Figure 11A:
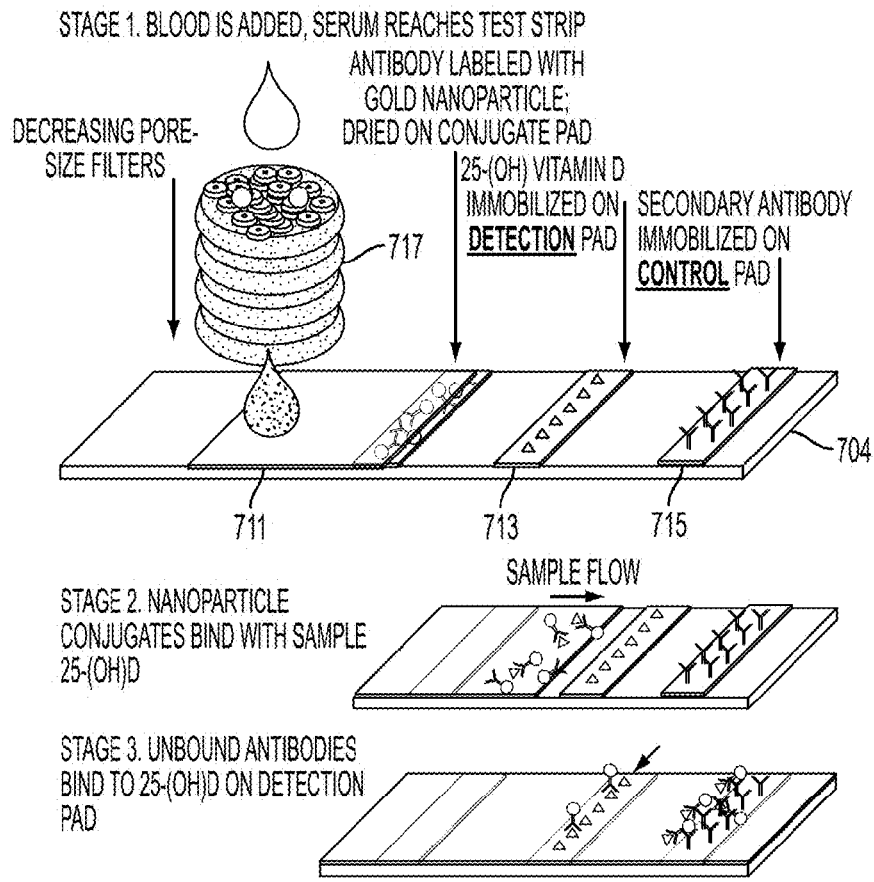
FIG. 11A schematically illustrates a nanoparticle based colorimetric test strip with details of a competitive Vitamin D assay including blood filtration.
Figure 11B:
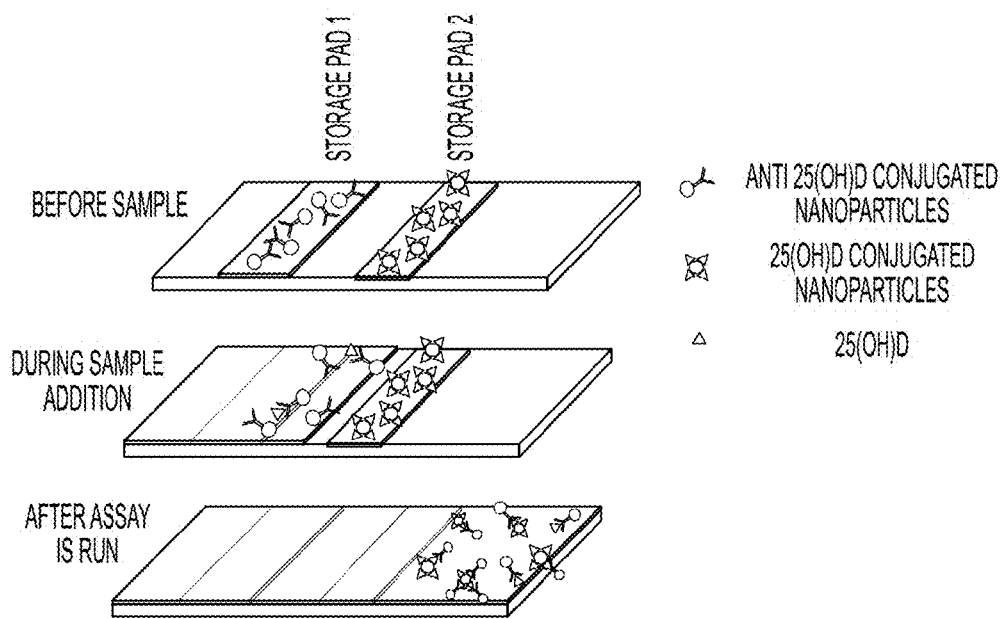
FIG. 11B shows a more detailed view of stages two and three from FIG. 11A, according to an exemplary aspect of the invention.

For standard pH indicator materials, it is not possible to determine the pH value from only one of the three RGB channels; moreover, an increase in the measured value of any one channel (e.g., only red) does not correspond to a linear increase in the pH of the sample. To simplify analysis and improve accuracy, the measured color can be transformed into an alternative color space that matches more closely to the indicator color trends. The median RGBA value for each 256×256 array is converted to the Hue-Saturation-Luminosity (HSL) color space by the standard conversion algorithm. In the HSL color space, the hue value is a single measurement from 0-360 that has been determined experimentally to vary approximately linearly with pH for common universal indicator materials (see FIG. 10).

For translation of the HSL values to the corresponding pH values, a calibration curve was determined using many titrations of buffers with known pH values. By comparing the median HSL value to this calibration curve, the pH of a sample can be reliably determined from the measured color. Because the holder shields the camera from external light fluctuations, the lighting conditions should in principle not vary greatly from image to image. Nevertheless, calibration data was used to account for the fluctuations that might inevitably persist, as well as to account for differences between individual smartphone cameras. For this reason, calibration sections were included in the disposable test strip that do not vary in color with changing pH. By analyzing these sections separately as described above, the HSL value for a calibration color can be determined on each measurement and compared directly with the expected value from the initial calibration. Due to the linearity of the pH with increasing H value, the calibration curve can be shifted to account for this difference, and the HSL-to-pH conversion for the sample section can be made more accurate. This calibration can be done accurately with a single calibration color, but additional calibration colors in other parts of the spectrum can be used for applications which require very high degrees of accuracy.

After the median HSL value is ultimately converted to pH with the calibration, this final pH value can be time- (and/or location-) stamped and stored in an external data file on the smartphone, which can be read in by the application later. Depending on the specific application, the pH measurement can also be correlated to another metric of interest prior to display and further analysis; for instance, for sweat hydration analysis, empirical testing of sweat composition in the literature has demonstrated a strong (r=0.79) correlation between pH and sweat sodium concentration. As reported, sodium concentration can be interpolated linearly from pH by pH=4+0.04*[Na+] (where the concentration in is millimolar). Similar relationships exist to correlate measured pH with a number of important metrics for both sweat and saliva analysis, and this final step can be easily modified accordingly so that the software can function in multiple diverse applications. FIG. 1 illustrates the exemplary method in a flow chart.

Advantageously, the entire process, from swiping the disposable strip to collect the sample through receiving the pH and/or sodium concentration measurement, need take only a few seconds, and the results can displayed on the smartphone screen for immediate user feedback. Because the data can also be time-stamped and stored, all of the measurements from a given run can be retrieved and the trend of the pH over time can be determined for additional information.

In addition to sweat, saliva is another body fluid that can provide important information on the user's health state. The pH of saliva, for example, has been shown to be influenced by diet. Monitoring salivary pH can be useful in preventing caries and maintaining good dental hygiene. Salivary pH can be measured in the same way and using the same device as for sweat pH. In addition, the calcium concentration in saliva can be an indicator of periodontitis, thus an embodied device could be used daily or routinely to monitor salivary pH and calcium concentration in order to maintain good dental hygiene.

Another application for a pH type device is for drug and alcohol abuse monitoring. For example, cocaine can be detected in sweat or saliva using several chemical and biochemical tests. Ethanol and fatty acid ethyl esters can also be monitored using chemical tests. This would allow users and health care professionals to track desintoxication progress and to monitor the risks of drug and alcohol abuse.

Another application is for the chemical detection of glucose in saliva. Glucose detection in saliva can be used as a fast, non-invasive test for people with potential risk of diabetes. This would allow people who have high blood glucose concentration to monitor their daily salivary glucose levels and adjust their diet accordingly.

Chemical tests can also be used to determine the presence of amino acids in sweat. This application could be important for detecting atopic skin conditions that might develop. Other areas of testing that currently rely on colorimetric pH indicator strips include soil testing, water testing for aquariums and swimming pools, and chemical experiments in secondary and tertiary education.

Figure 6:
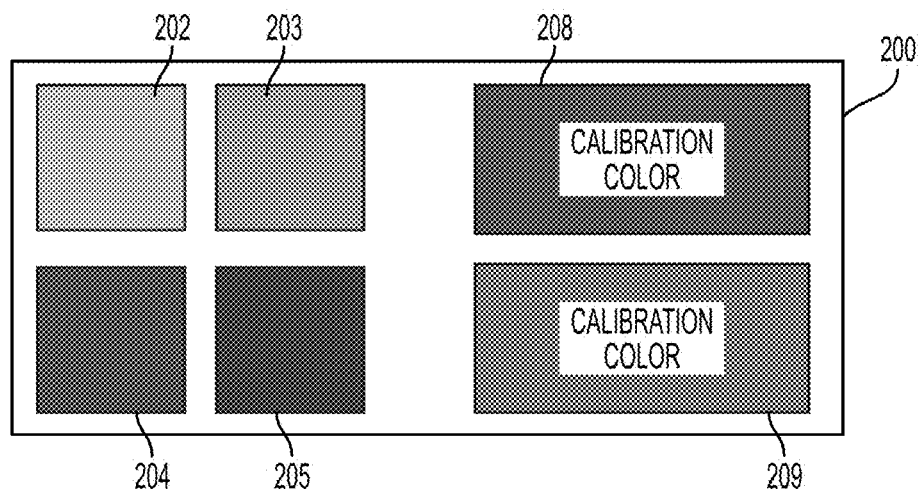
FIG. 6 schematically shows a disposable test strip used for pH measurements. The strip contains four colorimetric patches that can be compared for accurate pH measurements, and two constant colors for calibration, according to an illustrative aspect of the invention.

FIG. 6 illustrates a disposable test strip 200 having a test region that contains four separate colorimetric pH indicator regions 202, 203, 204, 205 and two constant colored plastic reference patches 208, 209 that do not vary with pH, which are used to calibrate away differences in light intensity and camera function from smartphone platform to smartphone platform.

Changes in light intensity while exercising can significantly change the colorimetric measurements made with the camera. It was found that the best way to maintain light uniformity while collecting data is to incorporate a light source in the system. There are three different methods/designs that are used to provide uniform illumination to the camera during data acquisition as illustrated in FIG. 4(a, b, c). A smartphone accessory housing 500 is shown in a cross sectional top plan view operationally attached to a smartphone. A first design shown in FIG. 4(a) provides a designed-in, indirect optical path that redirects the light from the resident smartphone flash 302 around a partial wall structure 348 in the housing so as to illuminate the rear surface 1002 of the test strip with diffuse light. An alternate design shown in FIG. 4(c) also makes use of the resident flash 302 of the smartphone to illuminate the test strip 1000. A light diffuser 308 is incorporated between the flash 302 and the front surface 1004 of the test strip in order to distribute the light from the flash evenly across the front surface of the test strip containing the test region 1008. A third design shown in FIG. 4(b) makes use of an LED 351 mounted in the housing 500 behind the test strip 1000 with a light diffuser 308 disposed between the LED and the rear surface 1002 of the test strip. The test strip illuminated uniformly with diffuse light. In this design, a battery 355 in the smartphone accessory provides external power to the LED 351 as illustrated in the inset in FIG. 8(a).

Another example of a smartphone system and method for quantitatively measuring salivary pH and sweat pH is presented. In this example, the test strips incorporate three different elements inserted in a 3D printed support: an indicator strip, a reference strip and a flash diffuser. The indicator strip consists of a 9 mm by 4 mm cutout of a pHydrion Spectral 5.0 to 9.0 plastic pH indicator strip for sweat testing and a 1.0 to 14.0 strip for saliva testing. The reference strip is made of white plastic material and is used in order to detect changes in white balance on the iPhone camera due to different light conditions or user error. The flash diffuser consists of a 2 mm thick membrane of polydimethylsiloxane (PDMS). Other suitable diffuser materials can also be used. The purpose of the flash diffuser is to reduce variations in the reading for different lighting conditions. It allows light from the smartphone's flash to diffuse and illuminate the rear surface of the test strip uniformly. In addition, the accessory is 3D printed using opaque Vera black material in order to isolate the test strip from variable external light.

The software app is illustrated in FIGS. 1 and 3 works as follows: First, upon loading the app, the user selects the test strip being used from a menu of different biomarker tests available, and the app loads the appropriate calibration data and user interface. Secondly, the user inserts the disposable test strip into the smartphone accessory and touches the "Analyze" function on-screen. Thirdly, the app turns on the camera flash and takes an image of the test strip. The quantitative analyte concentration is colorimetrically determined from the image and displayed on screen in under five seconds. If pertinent to the specific analyte, additional post-processing is also done from the results, and these results are displayed alongside the analyte concentration. Finally, by swiping left, a scatter plot of the results is generated to show trends over time. If desired, the data set can also be sent via email for later viewing or additional analysis.

Figure 5A:
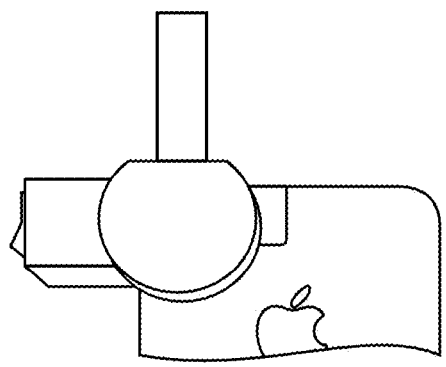
FIG. 5A schematically shows a smartphone accessory mounted on a smartphone including a test strip inserted therein.

Although the ubiquity of smartphones with high-quality integrated cameras makes such devices ideal for point-of-care biomarker detection, the wide range of variations across different devices and of test strip illumination present significant challenges to accurate colorimetric quantification. Other investigators have addressed this problem by calibrating for ambient light conditions through conversion to color spaces which are less sensitive to changes in brightness. On its own, this approach still requires uniform external illumination, and false colorimetric readings can be made if the smartphone is not placed at the proper distance from the test strip. One of the unique opportunities of smartphone-based colorimetric detection for portable diagnostics, however, is that image acquisition can instead be automated, so that the test strip is always held in the ideal position and imaged in the same manner, and the data is not easily affected by deviations in user protocol. Our device is isolated from ambient light with the smartphone accessory (e.g., FIG. 5a) and diffuses light from the smartphone camera flash for reproducible and uniform illumination, improving measurement accuracy and minimizing the potential for user error.

Similarly as stated above, although the image from the smartphone camera is initially defined with RGB (red green blue) values, individual red, green, and blue channels do not correlate well with pH over the range of a universal indicator strip. Nevertheless, the RGB values can be readily converted to an alternate color space that matches the color spectrum of the test strips more closely. We chose to convert to hue, which unlike RGB was found to monotonically increase with pH in our experiments over the entire range of the colorimetric test strips used. After an initial calibration to determine the relationship between the hue and the analyte concentration for each test strip, this single hue value is sufficient to quantitatively specify the color with a high degree of accuracy.

The process of image analysis is as follows. When the "Analyze" button is pressed, the smartphone app activates the camera flash, and an image is captured and stored first as an RGBA (red green blue alpha) byte array. The alpha channel, which is a measure of transparency, is discarded as it does not vary with analyte concentration. The RGB array is split into two sections—the first, corresponding to the upper colorimetric test strip, and the second, to a lower reference region of known color value which is used to compensate for variations between different smartphone cameras and from automated camera adjustment functions such as white balance. A 256×256 pixel square is selected from the center of each of these sections, and the hue value is calculated for each pixel from the RGB channels. The hue values are sorted, and the median value is chosen to minimize any remaining edge effects which are not removed by the PDMS flash diffuser. Because the color of the plastic reference section should not change between experiments if the device works correctly, the image acquisition process is restarted if the reference hue value varies from the expected calibration value by more than 5. This serves to eliminate the possibility of a user protocol error—if the test strip is inserted incorrectly and the strip is not optically isolated, the reference check will fail and the data will not be stored. If the reference check is passed, the test hue value is converted into an analyte concentration by means of a measured calibration curve and the relevant biological information is displayed on-screen immediately. A schematic of this process is shown in FIG. 1.

Figure 5B:
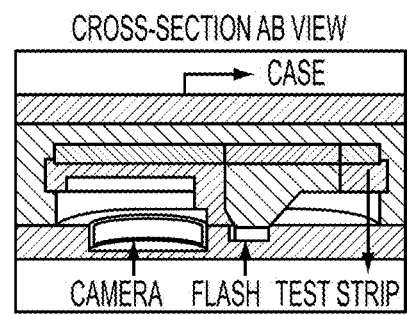
FIG. 5B shows a cross sectional view of the accessory for providing uniform illumination of a rear surface of a test strip to allow the test strip to be imaged consistently in different external lighting conditions, according to an illustrative aspect of the invention.

The correlation between hue and pH is built into the application, allowing users to run tests without additional calibration. This is possible because the accessory is designed in a way that minimizes the effect of external lighting as was previously discussed. FIG. 5b illustrates the design of the accessory housing around the camera and flash that allows for uniform lighting of the test strip. By guiding the flash light through the PDMS diffuser on the strip and behind the test strip, we avoid the need to build in a lighting element, such as an LED, that would make the system bulkier and require power input. The strip is imaged at a distance of 2.20 mm from the smartphone's camera and the whole optical piece has a depth of 4.90 mm. The relationship between hue and pH for our test strips was established using buffer solutions and a pH electrode (VWR SympHony SB70P) for an 8 point calibration. A third order polynomial was fitted through the data points in order to obtain a correlation between pH and hue. It was found that the variation between phones is the largest source of error, therefore defining the accuracy of the system over the range of physiologically relevant pH values to be within 0.2 pH units was useful.

In order to further improve the accuracy of our system, we incorporate a white reference strip on our test strip. A large variation in the hue value of the white reference indicates a failed measurement, possibly from a faulty or incorrectly inserted test strip. If the application detects an abnormal hue value, it rejects the data point and signals to the user to take another reading.

Although the system disclosed here was designed for and prototyped on the iPhone 4 and 4S, it could easily be ported to any other smartphone platform with a CMOS camera. Even if there are systematic differences in camera function and sensitivity between smartphones from different manufacturers, these differences can be corrected by calibrating the hue-to-pH conversion function once for each smartphone model used. If the hardware accessory is re-designed to fit over the camera and properly re-calibrated, the most important metric for determining the accuracy of the device should still be the variation between several phones of the same model, as described above.

Figures 7A, 7B:
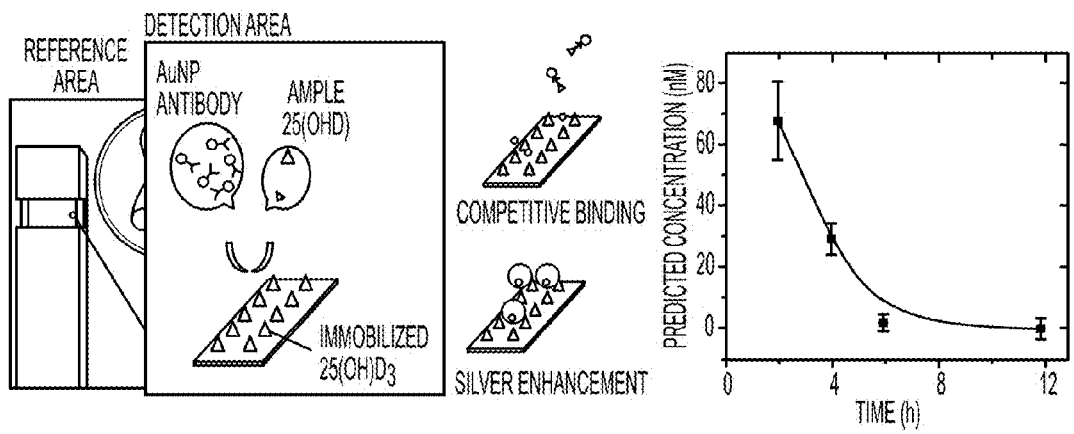
FIG. 7A shows a test strip consisting of two different areas that are imaged using the smartphone's camera: a gold nanoparticle-based detection area and a reference area. The detection area allows for a colorimetric reaction to occur when a sample of, e.g., sweat, saliva or blood is applied. The reference area consists of a uniform piece of polymer that does not change color when the sample is applied, according to an illustrative aspect of the invention.
FIG. 7B shows a variation in predicted concentration at different AuNP-anti-25(OH)D$_3$ incubation times on the detection area for 0 nM sample 25(OH)D, according to an illustrative aspect of the invention.

FIGS. 7(a), 9(a) and 9(b) illustrate gold nanoparticle (AuNP)-based test strips used to quantitatively measure vitamin D levels in a sample using a colorimetric competitive direct-antigen immunoassay according to an aspect of the embodied invention. This assay enables the quantification of 25(OH)D molecules whose small size (~400 g/mol) restricts their binding to more than one antibody at a time. 25(OH)D levels can be quantified by evaluating brightness differences between the detection area and a reference area on the test strip. The smartphone system can be used to quantify vitamin D levels by evaluating serum samples with unknown 25(OH)D concentrations.

Figures 8A, 8B:
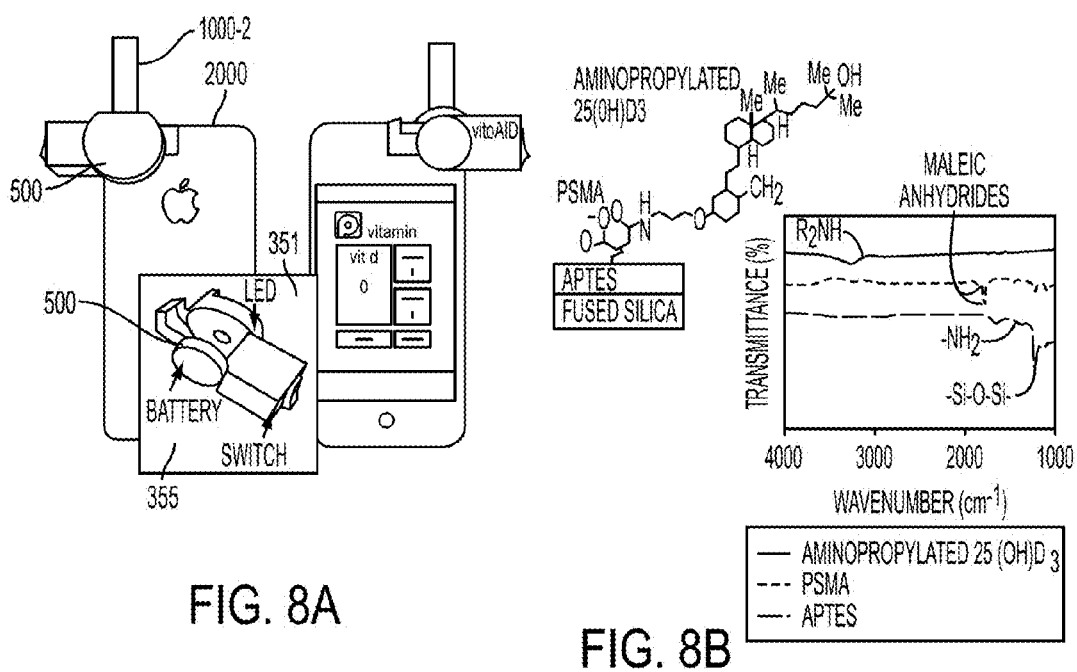
FIG. 8A shows a battery powered smartphone accessory with LED light source, on an iPhone, with the inset showing the components of the accessory.
FIG. 8B is a FT-IR spectra showing the chemical composition of the APTES, maleic anhydride, and aminopropylated 25(OH)D$_3$ layers that constitute the detection area of an illustrative test strip for quantitative Vitamin D measurements, according to an illustrative aspect of the invention.
Figure 12A:
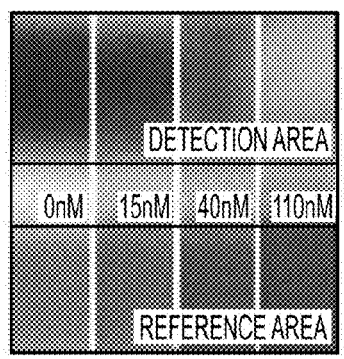
FIG. 12A shows colorimetric variation on the test strip of FIG. 11 at different known 25(OH)D concentrations.
Figure 12B:
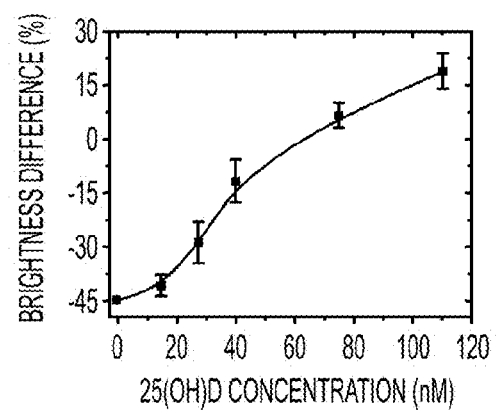
FIG. 12B calibration curve showing brightness difference between the detection area and reference area ΔH at different known 25(OH)D concentrations.
Figure 12C:
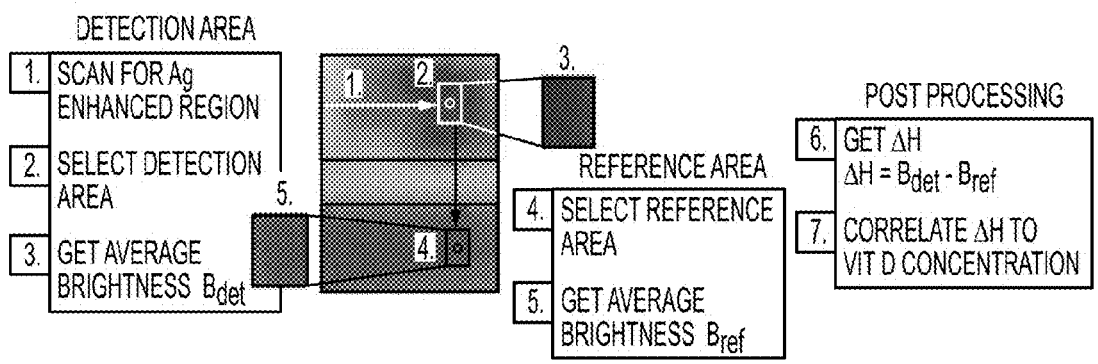
FIG. 12C shows an algorithm used in quantifying 25(OH)D levels on test strip, according to an illustrative aspect of the invention.

FIG. 8(a) illustrates an exemplary smartphone system that includes a smartphone 2000 loaded with a smartphone app and a smartphone accessory 500 attached to the smartphone. As described above, the smartphone accessory has been designed to minimize the effect of variability in external lighting conditions with an LED used to uniformly diffusely illuminate the rear surface of the test strip. The test strip 1002 was constructed and is composed of a detection area and reference area as illustrated in FIG. 12(c). The reference area allows the algorithm outlined in FIG. 12(c) to further adjust to differences in different smartphone platforms. The detection area that enables the colorimetric reaction to occur comprises a surface-immobilized layer of 25(OH)D on a fused Si-based substrate that serves as the detection area on the test strip. As shown in FIG. 8(b), 3-aminopropyltriethoxysilane (APTES) and polystyrene-co-maleic anhydride (PSMA) layers were sequentially coated on the fused Si substrate and aminopropylated 25(OH)D was covalently linked to achieve a stable 25(OH)D coating. In order to validate this method, the surface treatments were characterized by Fourier-transform infrared spectroscopy (FT-IR) as shown in the graph in FIG. 8(b). The initial introduction of APTES layer on the Si substrate is evident from the transmittance peak at 1654 cm' that is associated with primary amine groups ($-NH_2$). The PSMA coating was confirmed by the appearance of peaks at 1850 and 1780 $cm^{-1}$, which have been linked with maleic anhydrides in other studies. Lastly, the peak at 3300 $cm^{-1}$ corresponds to the formation of the secondary amine ($R_2NH$) bond between the PSMA and aminopropylated 25(OH)D and verifies the 25(OH)D immobilization.

The colorimetric reaction on the detection area of the test strip is based on a surface-based gold nanoparticle-based immunoassay as illustrated in FIGS. E(a) and 7. When a sample is applied onto the detection area of the test strip, only the antibody conjugates that are not bound to the 25(OH)D present in the initial sample are captured by the coated 25(OH)D on the surface. The colorimetric signals from the immobilized AuNP-antibody conjugates are then amplified using a silver enhancement scheme as the silver ions undergo reduction on the surface of the AuNP to increase their size and thereby increase the limit of detection of the system. For samples with high vitamin D levels, most of the antibody conjugates are occupied with 25(OH)D from the initial sample, resulting in only a subtle change in the colorimetric signal on the test strip. For samples with low vitamin D levels, the test strip develops an intense color that reflects the high number of antibody conjugates bound on the surface.

A critical step during testing is the incubation of the AuNP-anti-25(OH)D sample solution on the test strip's detection area. It is important to characterize the time it takes for the AuNP-anti-25(OH)D to immobilize in order to minimize the total assay time and to improve accuracy. In FIG. 7(b), we show the effect of different incubation times on the brightness difference between the detection and reference areas of the test strip ($\Delta H$) for a sample without 25(OH)D. After 6 h the brightness difference is within 10% of that obtained after a typical 12 h overnight incubation. This indicates that a 6 h incubation time is sufficient in order to obtain accurate results during such vitamin D measurements. The incubation time can however be significantly reduced by using the obtained negative exponential relationship to determine the minimum incubation time for ensuring that sufficient conjugate binding events have occurred on the detection area.

Once the competitive binding of AuNP-anti-25(OH)D was performed on the test strip, the quantification of the 25(OH)D levels in the initial sample can be achieved using the smartphone platform. First, the colorimetric change is captured using the smartphone's camera after inserting the test strip in the smartphone accessory. In FIG. 12(a) we show the colorimetric change in the detection region at different known concentrations of 25(OH)D. By comparing the differences in brightness between the detection area ($B_{det}$) and reference area ($B_{ref}$) we can estimate the concentration of 25(OH)D. In FIG. 12(b) we show that $\Delta H = B_{det} - B_{ref}$ can be correlated to the 25(OH)D concentration in the initial sample. A second order polynomial was then fitted onto this calibration curve in order to obtain a function such that $[25(OH)D] = f(\Delta H)$.

FIG. 12(c) shows the algorithm that allows the quantification of 25(OH)D across the entire range of physiological values. First, the detection area is scanned for silver enhanced regions where AuNP-anti-25(OH)D is bound. This is important because at higher 25(OH)D concentrations in the initial sample, the detection area rarely exhibits a uniform colorimetric change. A 100 px by 100 px area around the high intensity silver enhanced region is taken and the brightness is averaged across all the pixels in that area. The same steps are then performed on the reference region and an average brightness is calculated. Once the brightness difference between the detection area and the reference area is computed, the algorithm uses a second order polynomial $[25(OH)D] = f(\Delta H)$ derived from FIG. 12(b) to calculate the 25(OH)D concentration in the initial sample.

For a vitamin D deficiency test, once the sample has been acquired, several steps were performed in solution prior to its application onto the test strip. First, the filtered serum sample was mixed 1:10 (v/v) with 0.78 g/ml acetonitrile (Thermo Fisher Scientific Inc.) in order to liberate the 25(OH)D molecules that are in proportion of 95-99% bound to vitamin D binding proteins (DBP). The sample was then mixed with AuNP-anti-25(OH)D conjugate solution for 30 min. This ensures that all the 25(OH)D initially present in the blood sample is bound to AuNP-anti-25(OH)D before being applied onto the test strip.

The spherical AuNP (Nanopartz Inc., 30 nm) came pretreated with N-hydroxysuccinimide ester terminal (NHS) groups which specifically reacted with the primary amines of monoclonal anti-25(OH)$D_3$ IgG (Raybiotech Inc.) to form the AuNP-antibody conjugates. The antibody was first purified using the Pierce Antibody Clean-up Kit (Thermo Fisher Scientific Inc.) because 2% bovine serum albumin (BSA) stabilizers in anti-25(OH)$D_3$ are known to interfere with the amine-reactive conjugation. The antibody solution was placed into the Melon Gel-based purification support which binds non-antibody proteins while allowing the IgG antibody to flow through in a purified form during the one-minute centrifugation at 6000 g. The successful removal of BSA was checked by performing sodium dodecyl sulfate polyacrylamide gel electrophoresis (SDS-PAGE). For conjugation, the AuNP were mixed with the purified anti-25 (OH)$D_3$ at 0.1 mg/ml in 0.01 M amine-free phosphate buffer saline (PBS) buffer at pH 7.4. The mixture was sonicated for 30 s to re-suspend AuNP into solution, followed by vortexing for 30 min. at room temperature. The centrifugation was performed at 15000 g for 10 min. to remove the excess antibody in supernatant form and the final conjugates were reconstituted in 0.01 M PBS with 0.1% Tween-20 at pH 7.4.

The successful conjugation was confirmed through surface plasmon resonance changes using ultraviolet-visible spectroscopy. The conjugates were diluted to 10 μg/ml and stored at 4° C. until use.

The covalent immobilization of 25(OH)D was achieved by obtaining 25(OH)$D_3$, 3'-Aminopropyl Ether (Toronto Research Chemicals Inc.) and using its primary amines as linkers to the test strip surface. Immobilization of the peptides to surface using maleic anhydride chemistry has been demonstrated previously by others. Here, the aminopropylated 25(OH)$D_3$ was immobilized on a flat Si substrate other than on a typical well-plate which represents a compatibility improvement for use in our smartphone-based detection. Briefly, 4" fused Si wafers were cleaned in piranha solution, immersed in 20 mM APTES (Sigma-Aldrich Co. LLC) in isopropanol for 2 h and annealed at 120° C. for 1 h. The APTES coating acted as an activation layer for the binding of 1% PSMA (Sigma-Aldrich Co. LLC) dissolved in tetrahydrofuron, which was spin-coated at 3500 rpm for 30 s followed by curing at 120° C. for 2 h. The treated Si wafer was cooled and immersed in acetone for 10 min and subsequently diced into 4 by 7 mm strips. Finally, the 25(OH)D immobilization was achieved by incubating the PSMA-treated strips with 20 μg/ml aminopropylated 25(OH)$D_3$ in the coating buffer (0.1 M carbonate/bicarbonate buffer at pH 9.4) for 1 h at 37° C. The unreacted PSMA sites were treated by incubating the blocking buffer (0.01 M PBS with 1 mg/ml Casein and 0.05% Kathon preservative at pH 7.4) for 30 min at room temperature, and cleaned with washing buffer (0.01 M PBS with 0.05% Tween-20 at pH 7.4). The incubation procedures were performed in incubation chambers that housed the test strips and prevented pre-mature drying of the treatment solutions. The modified Si surfaces after each surface treatment were characterized by FT-IR using a Vertex 80-v spectrometer (Bruker Optics) equipped with a 60° germanium attenuated total reflection (VeeMax Ge ATR) crystal. For each spectrum, 256 scans at a spectral resolution of 4 $cm^{-1}$ were performed using a liquid nitrogen detector. After the 6 h incubation of AuNP-antibody conjugates with the sample on the detection area, the strip was rinsed three times with the washing buffer to remove unbound conjugates and incubated with silver enhancement solution from the Silver Enhancer Kit (Sigma-Aldrich Co. LLC). After 20 min, the detection area was rinsed with the washing buffer and air dried at room temperature.

We have demonstrated that we can measure physiological levels of 25(OH)D in solution with accuracy better than 15 nM and a precision of 10 nM. Moreover, the results obtained using the embodied invention are comparable with that of commercial ELISA kits. By analyzing three serum samples with unknown 25(OH)D concentrations, we were able to determine accurately the extent of vitamin D deficiency in each case.

In the disclosed method, we used a specific form of 25(OH)D for coating and detection, namely 25(OH)$D_3$ and anti-25(OH)$D_3$. The monoclonal anti-25(OH)$D_3$ has 68% cross reactivity with 25(OH)$D_2$ and 100% with 25(OH)$D_3$. The use of 25(OH)$D_3$ for the detection zone coating allows for the capturing of all the unbound AuNP-anti-25(OH)$D_3$ conjugates after the initial interaction with the sample.

An exemplary aspect of the invention is for cholesterol measurement. The embodied system can quantify cholesterol levels from colorimetric changes due to cholesterol reacting enzymatically on a dry reagent test strip. Again, a smartphone accessory allows uniform and repeatable image acquisition of the test strip, and is used in conjunction with an app that analyzes parameters such as hue, saturation, and luminosity of the test area, quantifies the cholesterol levels, and displays the value on the screen, as described herein.

FIG. 13(a) illustrates the smartphone accessory attached around the camera of the smartphone. It has been designed to allow quantification of the cholesterol colorimetric reaction that occurs on a dry reagent test strip over the entire range of physiological cholesterol values. The smartphone's flash is used to illuminate the strip. The utilization of the resident light source provides a robust system and the ability to deal with misalignment of the test strip, and it provides more uniform lighting for accurately imaging the colorimetric reaction on the test strip. Typical smartphone acquired images of the colorimetric reaction, at low (<100 mg/dl) and high (>400 mg/dl) cholesterol concentrations are shown at the bottom of FIG. 13.

In order to improve the sensitivity of the system to variations in the color of the test strip and to reduce the effect of test strip misalignment into the device, we incorporated a light diffuser over the flash as can be seen in the inset of FIG. 13(a). The effect of integrating different diffusers in the accessory housing on the measured saturation values at different points on the detection area is shown in FIG. 13(b). It can be seen that at low cholesterol concentrations a light diffuser is needed so that the color change can be quantifiable. When no diffuser is used or only PDMS is used, the strips appears as white with either 100% or 0% saturation levels. Diffusers made of black PDMS and FullCure, an acrylic-based photopolymer material, allowed for the saturation value on the low cholesterol test strip to be quantifiable with standard error of 0.16% and 0.42% respectively across a 200 px section at the center of the strip. This is important because it indicates that misalignment of the test strip will have little effect on the measured saturation value.

The sensitivity of the image acquisition system, defined as the ability to differentiate between colorimetric test strips at different cholesterol concentrations has also been investigated. As can be seen in FIG. 13(c), the accessory with the black PDMS diffuser has on average a 36.6% point decrease in lightness when imaging the high cholesterol test strip compared to the low cholesterol one. The effect is much lower, only 5.2%, when a FullCure diffuser is used. Consequently, black PDMS was used as the diffuser material because it not only allows for uniform illumination of the strip but also maximizes the range of colorimetric variation on the strip.

The test strips used in this example are dry reagent strips manufactured by CardioChek (Polymer Technology Systems Inc, IN, USA). When the user applies a drop of blood on one side, it first goes through a series of filter papers that separate plasma from red blood cells and direct some of the plasma towards an analyze-specific reaction pad. At that point, HDL is separated from LDL and VLDL fractions and precipitated by the reaction with phosphotungstic acid. An enzymatic reaction then converts total cholesterol and HDL cholesterol to cholest-4en-3-one and hydrogen peroxide. The peroxide then reacts with disubstituted aniline to form quinoneimine dyes7. The color change from the last reaction is then imaged inside the smartphone accessory by the smartphone camera.

In order to quantify the colorimetric reaction and to obtain the blood cholesterol concentration value, we developed a calibration curve linking cholesterol to the HSL (Hue Saturation Lightness) cylindrical coordinate representation of the RGB (Red Green Blue) color values at the center of the cholesterol test strip. Hue (II) has a piecewise definition and in the region of interest of the cholesterol colorimetric reaction can be written as a function of the red (R), green (G) and blue (B) color values:

$$H=(B-R)/C+2 \text{ if } M=G \text{ or } H=(R-G)/C+4 \text{ if } M=B.$$

In the equation above, C=M-m where M=max(R,G,B) and m=min(R,G,B). In addition, the lightness (L) and saturation (S) are described by the following equations:

$$L=\tfrac{1}{2}(M+m)$$

$$S=(M-m)/(1-|2L-1|).$$

Figure 15A:
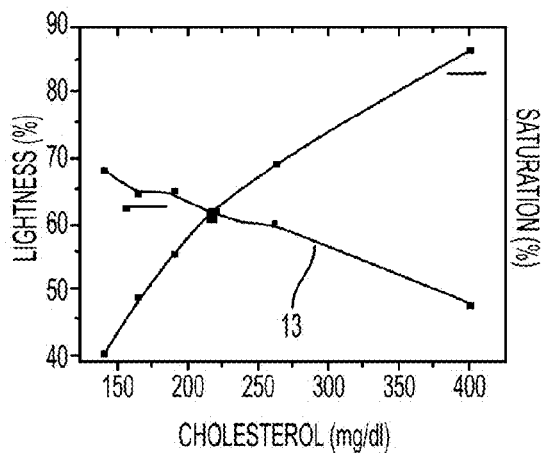
FIG. 15A shows variation in lightness (13) and saturation (black) vs. cholesterol levels.

For the calibration curve, human serum is used and augmented using Cholesterol Lipid Concentrate in order to cover the whole range of physiological cholesterol levels. At each cholesterol concentration in the relevant physiological range (140 mg/dl to 400 mg/dl) the test strip was first analyzed using the CardioChek portable Blood Test System and then imaged using the smartphone system. FIG. 15(a) shows the variations in lightness and saturation for images acquired using the smartphone system. The cholesterol reading is first obtained using the CardioChek portable Blood Test System. The hue values showed very little variation across the whole range of cholesterol values. However, hue values can be used to indicate if a test is successful or if it fails due to image acquisition or test strip issues. The relationship between concentration and saturation can be described by a second order polynomial, $$[\text{Chol}]=0.08S^2-4.56S+196.84.$$

Figure 15B:
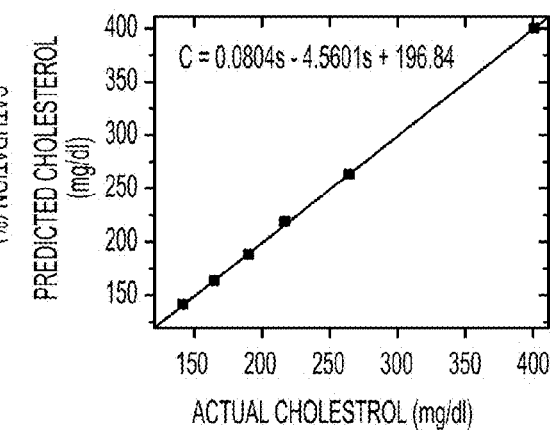
FIG. 15B predicted cholesterol concentration versus actual cholesterol concentration defined by CardioCheck PA, according to an illustrative aspect of the invention.
Figure 19:
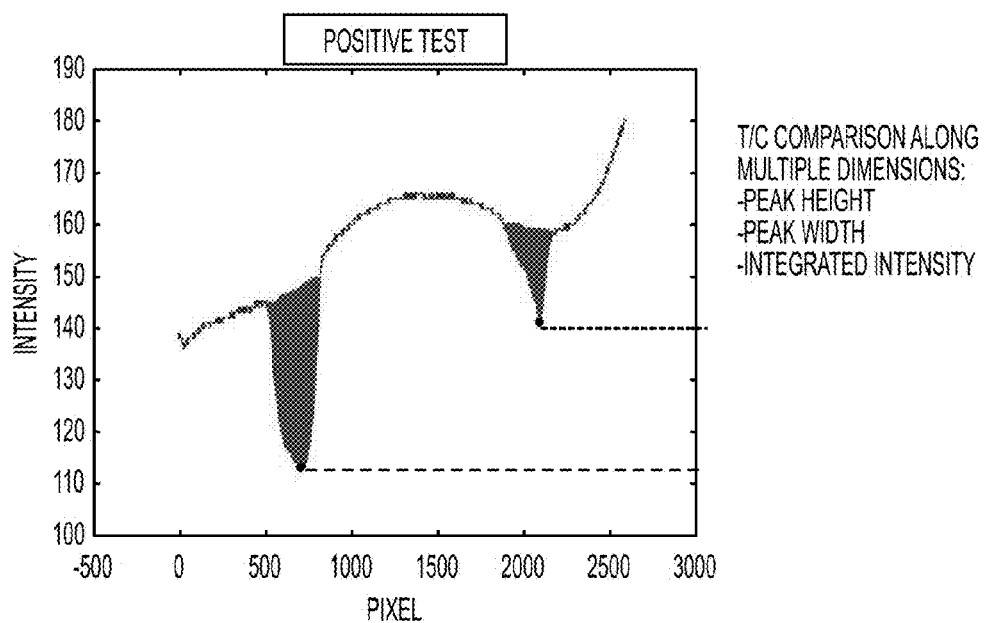
FIG. 19 is a graph showing test and control (T/C) line comparisons along multiple dimensions, according to an illustrative aspect of the invention.

As can be seen in FIG. 15(b), this allows almost perfect matching with a maximum error of 1.8%.

Figure 2B:
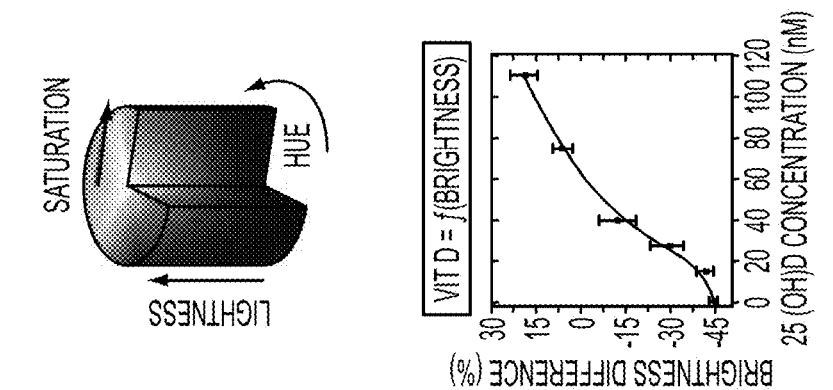
FIG. 2B shows the relationship between different analytes and hue, saturation and luminosity parameters, according to an illustrative embodiment of the invention.
Figure 2A:
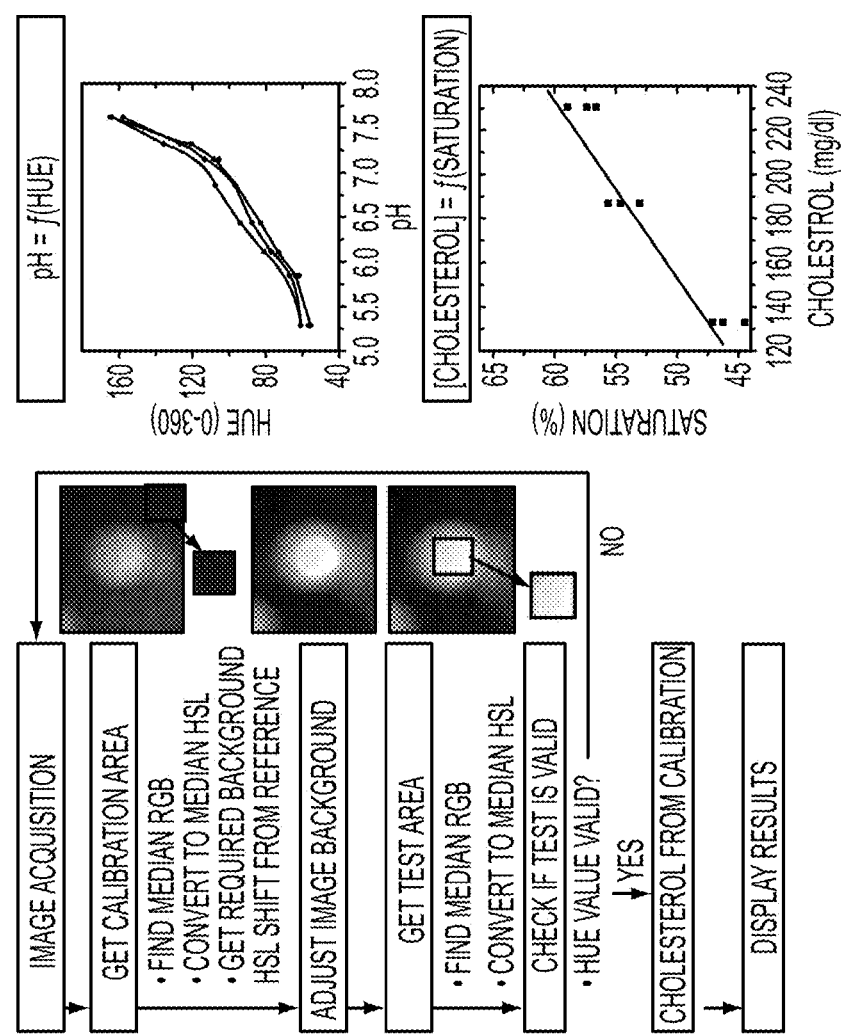
FIG. 2A shows the steps of extracting the hue, saturation and luminosity of both a reference area and a detection area on a test strip, and quantifying an analyte concentration using a calibration curve, similar to that of FIG. 1.

The software app used in this example is illustrated in FIG. 2. When the user presses "analyze" on the app, an image of the colorimetric color changes is acquired through the iPhone camera. The app then executes several processing steps before the cholesterol value is displayed on the smartphone screen. First, a 100 px by 100 px calibration area is selected at the bottom right corner of the image. The average RGB value is computed and converted to HSL. This average HSL value is then compared to a reference value and a background shift is computed. The whole image is then is subjected to this background shift. After the background shift, a 100 px by 100 px area in the middle of the detection circle is selected and the same computation as before is done to obtain the average HSL value of the test area. The algorithm then verifies if the test is valid by comparing the average hue value to the typical value of the cholesterol test, which is constant across physiological cholesterol values (H~180) both for serum samples and blood samples during test trials. In order to decrease fluctuations due to lighting conditions, the strip is imaged three times and the average hue value over those three images is taken. If the hue value falls within the range of expected hue values, then the cholesterol level is calculated using the calibration curve previously obtained. The ability of identifying bad samples is a major advantage over other specialized hand-held devices that use reflectance photometry to quantify colorimetric reaction.

Figure 14A:
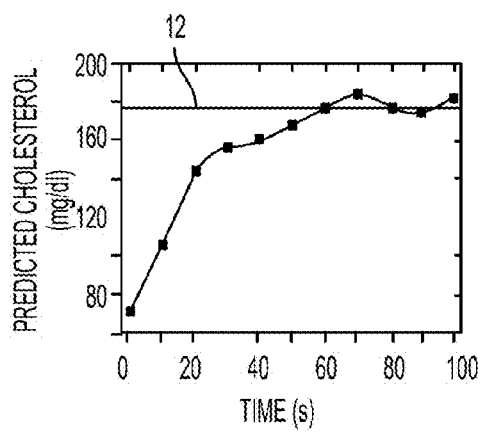
FIG. 14A shows variations in predicted cholesterol levels vs. time for a test strip with the solid horizontal line representing the actual cholesterol level of 178 mg/dl.
Figure 14B:
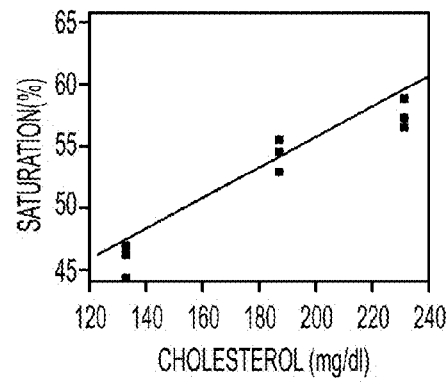
FIG. 14B shows variation in readings with different three different iPhones.
Figure 14C:
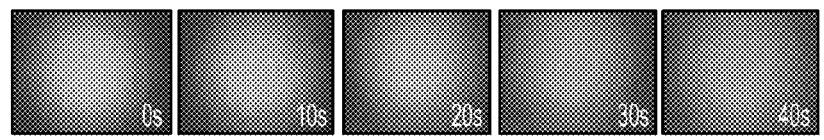
FIG. 14C shows the imaging of the test strip during the first 40 s; according to an illustrative aspect of the invention.

A critical issue to consider for point-of-care testing is the accuracy of the measurement. Once the user applies a drop of blood on the strip it takes some time for the colorimetric change to occur on the other side of the strip since the blood goes through several separation steps and chemical reactions and the colorimetric change occurs gradually as can be seen at the bottom of FIG. 14. If the strip is imaged before the reaction has terminated then we will get a misleadingly low value for the blood cholesterol level. In order to determine the approximate time required for the reaction to occur we have monitored the color change for a serum sample with an actual concentration of 178 mg/dl. As can be seen in FIG. 14(a), it takes about 60 s for the colorimetric change to stabilize. The variation in predicted cholesterol levels are contained within less than 3.9% of the actual value after that; however, the value shifts up as time elapses. It is therefore important to be consistent by building in the algorithm a time frame for imaging the test strip. In addition, averaging several acquired images during that time frame can help further improve the accuracy.

Embodiments of the invention are related to a smartphone apparatus, a smartphone accessory, a method for obtaining a point-of-collection, selected qualitative and/or quantitative indicia of an analyte on a test platform, and a portable, modular, point-of-collection, colorimetric-based diagnostic system including the aforementioned smartphone, smartphone accessory, and an executable application resident in the smartphone enabling/performing the aforementioned method, as further described herein below. Exemplary aspects include a smartphone-based platform for qualitative and/or quantitative readout of lateral flow immunochromatographic assays, and associated methods and applications.

The smartphone platform includes an accessory 1602 as shown in FIG. 16(A, B, C) that attaches to the smartphone camera (not shown), and consumable lateral flow tests (strips) 1604 (not part of the invention per se) that are inserted into the accessory. A smartphone application ("app") 1707 (FIG. 17(B)) operates the smartphone camera, interprets the results automatically, displays the results to the user, and archives them to enable long term tracking.

In the embodiment described herein above for colorimetric analysis as applied, e.g., to cholesterol monitoring, the color change of the test strip was accurately obtained without providing a focused image of the region of interest. For the instant embodied aspect for the readout of lateral flow assays, it is advantageous to obtain magnified and focused images of the test region as both the color intensity and the shape (line shape, width etc.) of the signal lines developed are of interest. The instant aspect thus includes a lens 1612 to focus and magnify the test strip region of interest, and a LED 1614 to ensure consistent illumination for imaging, as shown in FIG. 16(C). The battery 1617 (FIG. 16(B)) powers the LED and the switch 1618 enhances the efficiency of the LED operation by allowing the user to turn on the LED only during operation. The test strip holder accepts the lateral flow test strips and includes a cap 1620 (??) to enclose the sample collection pad after the strip is exposed to the sample.

Example

The inventors have developed a first generation smartphone prototype for reading lateral flow test strips and accurately determining the number of colorimetric lines that develop, thereby being able to distinguish between a positive and a negative result. Here the preliminary performance of the smartphone technology was demonstrated using the lateral flow assays for human chorionic gonadotropin (hCG), widely known as pregnancy tests.

To conduct the preliminary test for hCG, the user first attaches the accessory 1602 to the smartphone 1701. Their alignment is such that the built-in lenses of the smartphone and the accessory lens are aligned for enhanced imaging. Upon dipping the test strip in a sample and capping the collection end to prevent contamination, the user inserts the test strip into the accessory as shown in FIG. 17(A). A mechanical stopper mechanism (not shown) is incorporated into the design of the test strip holder and the accessory such that the region of interest on the test strip is positioned consistently across different test strip insertion processes. Next, the user opens the smartphone 'app' 1707 and selects the desired test, as suggested in FIG. 17(B). The "analyze" button 1711 of the final screen 1712 initiates a count-down (e.g., 3 minutes for hCG tests), after which a magnified and focused image of the test strip is captured and processed by the 'app' before the results are displayed to the user.

After an image is captured by the smartphone app, it is then filtered and processed to optimize the limit of detection and improve accuracy over normal visual inspection. The grayscale intensity of the raw image was found to be not sufficient to accurately distinguish a shallow control line from the background. To ensure accurate detection of the test line, a series of image processing steps are performed to improve the signal to noise ratio and allow for automatic line detection.

A schematic overview of the image processing algorithm is shown in FIG. 18(A). First, a 3×3 Gaussian filter 1802 is applied to the raw image to smooth out some of the noise. The image is then converted to the Hue Saturation Luminosity (HSL) color space 1804 so that the hue channel can be used as a single-channel measurement that distinguishes the background from the colorimetric lines. The hue of the colored control and test lines are lower than the hue of the background, so that the presence of a line can be detected by finding a local minimum in the hue data. After the color space conversion, the 2D image is reduced to a 1D array 1805/1806 by replacing each row in the 2D image with the median hue value along that row. The median filtering reduces the noise, and the lower dimensionality reduces the process of peak detection to a 1D digital signal processing problem.

The local minima 1809 corresponding to the test 1807 and control 1808 lines are now located by stepping through the 1D array and storing all points which are at least 10 hue values below the last inflection point on both sides. The number of detected minima yields binary test results: for negative tests, only one line should be detected (FIG. 18(C)), and for positive tests both the control and test lines should be detected (FIG. 18(B)). Although the test strip is designed for qualitative binary results, the relative shape and magnitude of the two detected peaks can also be compared to give quantitative data about the analyte concentration, which would be inaccessible without the image analysis software.

One of the key advantages of the image processing analysis over visual inspection is that the testing protocol can be controlled carefully to minimize user error. Because the colorimetric reaction is only valid over a certain time interval, the test strip protocol requires that the results be discarded if taken before or after an optimal three minute window. Using the device presented, however, every measurement is taken at the same controlled time after the test strip is inserted, removing the possibility of accidentally falling outside the allowed window.

The device can also ensure quality measurements by checking for test strip errors and misalignment during the analysis. For a test to be valid, the control line must be visible; if no peak is detectable in the appropriate region on the image, either the test strip did not develop properly, or the strip is misaligned in the device. In either case, the software app will reject this measurement and give a warning that a new test strip should be used. This reduces the possibility of a false negative result. Similarly, the relative magnitude of the test and control lines (T/C ratio) is an indication of the concentration of the analyte. Because the T/C ratio can be calculated during the analysis, positive test results that result in too low a T/C to be statistically significant can be repeated to minimize the possibility of false positive results.

The embodied device uses a focusing lens 1612 to magnify the image of the strip and an LED 1614 for uniform illumination. It would also be possible to eliminate the externally powered LED and instead use an alternate light source such as the built-in smartphone camera flash (not shown). This would lower the complexity of the device but also remove a degree of control over the lighting conditions across smartphone models and platforms. It would also be possible to modify (or remove) the focusing lens by changing the optical path length of the device, which would again lower the complexity but increase the size of the device to make it less portable.

In principle, the detection mechanism disclosed herein would be applicable to any colorimetric lateral flow assay with distinct test and control lines that can be observed. While the use of a dedicated device with image processing software is not necessary in all cases, there are a certain class of applications that require high accuracy and high security where such an approach is highly advantageous. The device presented has a number of checks in place to safeguard against errors in both the user protocol and in the test strip manufacturing itself, and the results of the test are stored instantaneously and cannot be altered by the user. In the context of law enforcement or work place drug screening, for instance, this added security protects against tampering with the data, as well as costly false positive results. The device also has several key advantages for medical diagnostics due to the increased accuracy at making qualitative (binary) measurements, as well as the enablement of quantification. Data security and confidentiality are also major concerns in a hospital or clinical environment, which is another benefit of using a digital reader that can be easily connected to a HIPAA-compliant database for secure long-term storage.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

TABLE 1

| | Application(s) | Target | Quantification Required | Fluid |
|---|---|---|---|---|
| Basic Electrolytes | Basic Metabolic Panel (Many Diagnosis) | Sodium (Na) | Yes | Blood |
| | Basic Metabolic Panel (Many Diagnosis) | Potassium (K) | Yes | Blood |
| | Basic Metabolic Panel (Many Diagnosis) | Chloride (Cl) | Yes | Blood |
| | Basic Metabolic Panel (Many Diagnosis) | Bicarbonate (Dissolved $CO_2$) | Yes | Blood |
| Kidney Function Tests | Kidney Function | Urea (Blood Urea Nitrogen, BUN) | Yes | Blood |
| | Kidney Function | Creatinine | Yes | Blood |
| Protein Tests (useful for Kidney and Liver Problems) | Kidney and Liver Function | Serum Calcium | Yes | Blood |
| | Kidney and Liver Function | Serum Total Protein (TP) | Yes | Blood |
| | Kidney and Liver Function | Human Serum Albumin | Yes | Blood |
| Liver Function Tests | Liver Function | Bilirubin | Yes | Blood |
| | Liver Function | Alkaline phosphatase (ALP) | Yes | Blood |
| | Liver Function | Aspartate amino transferase (AST or SGOT) | Yes | Blood |
| | Liver Function | Alanine amino transferase (ALT or SGPT) | Yes | Blood |
| Cholesterol Test Panels | Atherosclerosis, Coronary Disease, High Cholesterol | Total Cholesterol | Yes | Blood |
| | Atherosclerosis, Coronary Disease, High Cholesterol | HDL | Yes | Blood |
| | Atherosclerosis, Coronary Disease, High Cholesterol | LDL | Yes | Blood |
| | Atherosclerosis, Coronary Disease, High Cholesterol | Triglycerides | Yes | Blood |
| General Tests and Miscellaneous | Diabetes, Basic Metabolic Panel (Many Diagnosis) | Glucose | Yes | Blood |
| | | Calcium (Ca) | Yes | Blood |
| | Osteoporosis, Basic Metabolic Panel (Many Diagnosis) | C Reactive Protein | Yes | Blood |
| | | Hemoglobin A1C | Yes | Blood |
| | Inflammation | Chloride | Yes | Sweat |
| | Diabetes, Long term high glucose | pH | Yes | Sweat |
| | Cystic Fibrosis Dehydration | androgens (DHEA, testosterone) | Yes | Saliva |
| | Hypogonadism Allergies | allergen-specific IgA | No | Saliva |
| | Diagnosis of PCOS, hormonal imbalance | Testosterone | Yes | Saliva |
| | Renal Injury in HIV+ Patients | β-2-microglobulin (β2MG) | Yes | Urine |
| | | TNF-like weak inducer of apoptosis | Yes | Urine |
| | Lupus | HBV surface antigen | Yes | Saliva |
| | Hepatitis | anti-HCV | Yes | Saliva |
| | Hepatitis | melatonin | Yes | Saliva |
| | Pineal Physiology in newborns | uroporphyrin, coproporphyrin | Yes | Urine |
| | Prorphyria | sweat proteins[1] | Yes | Sweat |
| | Schizophrenia Intoxication | Fatty acid ethyl esters | Yes | Sweat |
| | Liver Disease | parasite Entamoeba histolytica | Yes | Saliva |
| | Tissue Damage | lactate, chloride, urea, and urate | Yes | Sweat |

TABLE 1-continued

| | Application(s) | Target | Quantification Required | Fluid |
|---|---|---|---|---|
| Heart Attack Panel | Myocardial Infarction (heart attack) | Troponin | Yes | Blood |
| | Myocardial Infarction (heart attack) | Myoglobin | Yes | Blood |
| | Myocardial Infarction (heart attack) | CK-MB | Yes | Blood |
| | Myocardial Infarction (heart attack) | C Reactive Protein | Yes | Saliva |
| Blood Clotting Tests | Prothrombin Time and INR | Prothrombin Time and INR | Yes | Blood |
| | Clotting Problems, Cardiovascular Disease, Inflammation | Fibrinogen | Yes | Blood |
| Cancer Tests | Prostate Cancer | sarcosine | Yes | Urine |
| | Prostate Cancer | prostate cancer antigen 3 (PCA3) | Yes | Urine |
| | Prostate Cancer | Prostate-Specific Antigen (PSA) | Yes | Blood |
| | Ovarian Cancer | Estrogen | Yes | Saliva |
| | Bladder Cancer | NMP22 | Yes | Urine |
| | Breast Cancer | Lipid peroxides | Yes | Saliva |
| | Breast Cancer | tumor suppressor protein p53 | Yes | Saliva |
| | Oral Cancer | transferrin | Yes | Saliva |
| | Oral Cancer | Cyclin D1/Maspin | Yes | Saliva |
| | Pancreatic Cancer | mRNA biomarkers | Yes | Saliva |
| Vitamin Tests | Bone Health, Osteoporosis, Cancer, Depression | vitamin D | Yes | Blood |
| | Pregnancy, Neural Tube Defects | Folate | Yes | Blood |
| | vitamin C levels | vitamin C | Yes | Urine |
| | Many other vitamin tests can be performed colorimetrically | vitamin B12, vitamin A, etc. | Yes | Blood |
| Hormone and Steroid Tests (Including Thyroid Function Tests) | Cardiovascular Health, | DHEA | Yes | Blood, Saliva |
| | Reproductive Health elevated in hypothyroidism & decreased in hyperthyroidism disorders associated with testosterone abnormalities | Thyroid Stimulating Hormone (TSH) | Yes | Blood |
| | Ovarian Activity and health | Testosterone (Free) | Yes | Blood |
| | A number of other tests also exist | Estradiol | Yes | Blood |
| Infectious Disease | Sexually Transmitted Infection | | | |
| | AIDs, viral Infection | Chlamydia (anti-LPS) HIV | No | |
| | Toxoplasma gondii infection | IgM and gG antibodies | No | Saliva, Blood |
| | Helicobacter pylori Infection | IgM and gG antibodies | Yes | Saliva |
| | Many other infections | IgM and gG antibodies | Yes | Saliva |
| Other electrolytes and minerals | General Testing | pH | Yes | Blood |
| | General Testing | Copper | Yes | Blood |
| | General Testing | Iron | Yes | Blood |
| | General Testing | Phosphate | Yes | Blood |
| | General Testing | Ammonia | Yes | Blood |
| | General Testing | Lithium | Yes | Blood |
| | General Testing | Magnesium | Yes | Blood |
| Substance Levels (i.e. Drugs) | Check Dosage | Acetaminophen(Tylenol) | Yes | Blood |
| | Cannabis use | Cannabinoids | No | Blood, Urine |
| | Drug use (one test for multiple targets) | Ecstasy, Heroin, Cocaine, and others | Yes | Blood, Urine |
| | Drug use | 6-monoacetylmorphine | | Saliva |
| | Drug use | amphetamine | No | Saliva |
| | Drug use | methamphetamine | No | Saliva |
| | Drug use | N-desmethyldiazepam | No | Saliva |
| | Alcohol Use | ethanol | No | Saliva |
| | Drug use | opiates, methadone, morphine, benzodiazepines | Yes | Urine |

TABLE 1-continued

| | Application(s) | Target | Quantification Required | Fluid |
|---|---|---|---|---|
| Pregnancy Related Targets | Ovulation Testing | hCG | Yes | Urine |
| | Ovulation Testing | luteinizing hormone (LH), E3G | Yes | Urine |
| | Ovulation Testing | luteinizing hormone (LH) | Yes | Saliva |
| Diabetes Measurements | Diabetes, Basic Metabolic Panel (Many Diagnosis) | Glucose | Yes | Blood |
| | Diabetes | chromogranin A | Yes | Saliva |
| Urine Test Strips (Siemens) | Carbohydrate Disorders like Diabetes | Glucose | Improves Test | Urine |
| | Liver Disease and Jaundice | Bilirubin | Improves Test | Urine |
| | | Ketone (Acetoacetic Acid) | Improves Test | Urine |
| | Carbohydrate Disorders like Diabetes | Specific Gravity | Improves Test | Urine |
| | Measure of Kidney Function for General Disease | Blood | Improves Test | Urine |
| | | pH | Improves Test | Urine |
| | Most often used to notice trauma to kidneys | Protein | Improves Test | Urine |
| | Multiple uses, lung and kidney function, therapeutic uses Should be low, higher can indicate nephropathy of multiple locations Liver Function | Urobilinogen | Improves Test | Urine |
| | Urinary Tract Infection | Nitrite | Improves Test | Urine |
| | Urinary Tract Infection | Leukocytes | Improves Test | Urine |
| Dental Applications | Periodontitis | pH | Yes | Saliva |
| | Periodontitis | peroxidase | Yes | Saliva |
| | Periodontitis | hydroxyproline | Yes | Saliva |
| | Periodontitis | calcium | Yes | Saliva |
| | Pregnancy gingivitis risk | estrogens | Yes | Saliva |
| Dermatology Applications | atopic skin conditions | free amino acid composition | Yes | Sweat |
| Depression | Stress Level | Cortisol | Yes | Urine |
| | Stress Level | Cortisol | Yes | Saliva |
| | Major depressive disorder (MDD) | pro-inflammatory cytokines and neuropeptides | Yes | Sweat |
| | Major depressive disorder (MDD) | adiponectin, leptin, ACTH and cortisol secretion | Yes | Sweat |
| | Stress Related | neuropeptide Y | Yes | Sweat |
| Other Iron Panel Tests | | | | |

We claim:

1. A method performed by an imaging system for obtaining a point-of-collection, selected qualitative and/or quantitative indicia of an analyte on a test platform, comprising:
   providing a modular assay test platform (e.g., test strip) having at least one test region and a control region;
   providing an analyte to be tested on the at least one test region;
   providing an imaging system to implement the steps of:
      obtaining an image of the at least one test region containing the analyte and the control region;
      selecting an array of pixels in the image of the at least one test region containing the analyte and the control region;
      determining a Red-Green-Blue-Alpha color value for each of the arrays of pixels;
      extracting a test image region for analysis;
      converting the Red-Green-Blue-Alpha array to an alternate color space as determined by the specific test including at least one of Hue-Saturation-Luminosity, Hue-Saturation-Value, and greyscale;
      determining one of a median, mean, maximum, minimum, or other statistical measure of the color or intensity value for various regions of the test platform containing test and control areas and creating a one dimensional array containing these values;
      determining a low-frequency variation in color or intensity value over the array and,
      performing illumination correction and background subtraction;
      detecting a peak or valley in the adjusted array corresponding to the test and control regions to be measured;
      determining a depth, width, height (for example, based on intensity or color maxima/minima), and/or area (for example, based on integrated color or intensity) of these peaks or valleys which correspond to detection or control regions of the test platform; and
      determining a qualitative presence of the selected indicia of the analyte by the number of peaks or valleys present, and/or a quantitative value of the selected indicia of the analyte by quantitative comparison of two or more peaks or valleys.

2. The method of claim 1, wherein the assay test platform is sensitive to at least one of a chemical colorimetric reaction, an enzymatic colorimetric reaction, and a gold nanoparticle colorimetric reaction, including a lateral flow type immunoassay.

3. The method of claim 1, wherein the assay test platform is a disposable lateral flow immunochromatographic test strip.

4. The method of claim 1, comprising obtaining the image of the at least one test region containing the analyte and the control region using the imaging system, wherein the imaging system includes a light source and an image detector.

5. The method of claim 4, further comprising displaying the determined selected indicia of the analyte on a smartphone.

6. The method of claim 4, wherein the imaging system further comprises a smartphone accessory that includes:
   a housing that can be removeably attached to a smartphone in a manner that at least optically couples the smartphone accessory to a resident smartphone camera;
   a lens that allows for adjustment of the focal length of the smartphone camera to enable imaging of the test platform in a compact device,
   wherein the housing is opaque such that the smartphone accessory is substantially externally light-tight when the test platform is disposed therein,
   further wherein the housing includes at least one of a designed-in optical pathway and a light diffuser in the housing for providing diffuse illumination of a surface of the test platform disposed therein from an internal light source resident in the housing or an external light source resident in the smartphone to which the smartphone accessory can be attached.

7. The method of claim 6, wherein the light source is one of an internal smartphone flash source and an external light-emitting diode source.

8. The method of claim 4, further comprising at least one of time stamping and location stamping the determined selected quantitative indicia of the analyte and storing the determined value for future access.

9. The method of claim 8, comprising storing the time and/or location data in at least one of a readable file in a smartphone, an external readable file, and in a Cloud file.

10. The method of claim 8, further comprising determining a temporal and/or a location trend of a plurality of the determined selected quantitative indicia of the analyte.

11. The method of claim 4, further comprising correlating the determined selected quantitative indicia of the analyte to a related selected metric and displaying a value of the related selected metric on a smartphone.

12. The method of claim 1, wherein the analyte is one of sweat, saliva, blood, tears, urine, and other bodily fluids.

13. The method of claim 6, wherein obtaining the image of the test region or regions containing the analyte and the control region or regions further comprises illuminating a surface of the test platform that is illuminated by the light source with diffused light from the light source.

14. The method of claim 1, wherein the step of obtaining the image of the test region or regions containing the analyte and the control region or regions comprises illuminating a surface of the modular, colorimetric test platform.

15. The method of claim 4, wherein the imaging system comprises a brand-independent or operating-system-independent smartphone.

16. The method of claim 1, wherein obtaining an image of the at least one test region comprises obtaining multiple images denoting changes in the indicia over time, which can be used to provide an improved estimate of the initial concentration of the analyte.

17. The method of claim 1, wherein obtaining an image of the at least one test region comprises obtaining multiple images denoting changes in the indicia over time, which can be used to serve as a method for detecting an error with the test.

18. A portable, modular, point-of-collection, colorimetric-based diagnostic system, comprising:
   a smartphone including an image detector;
   a smartphone accessory comprising:
      a housing that can be removeably attached to the smartphone in a manner that at least optically couples the smartphone accessory to a resident smartphone camera;
      a lens that allows for adjustment of the focal length of the smartphone camera to enable imaging of the test strip in a compact device,
      wherein the housing is opaque such that the smartphone accessory is substantially externally light-tight when a test strip is disposed therein,
      further wherein the housing includes at least one of a designed-in optical pathway and a light diffuser in the housing for providing diffuse illumination of a surface of the test strip disposed therein from an internal light source resident in the housing or an external light source resident in the smartphone to which the smartphone accessory can be attached; and
   an executable application resident in the smartphone that, in operation, performs the following steps:
   obtaining an image of the at least one test region containing the analyte and the control region;
   selecting an array of pixels in the image of the at least one test region containing the analyte and the control region;
   determining a Red-Green-Blue-Alpha color value for each of the arrays of pixels;
   extracting a test image region for analysis;
   converting the Red-Green-Blue-Alpha array to an alternate color space as determined by the specific test including but not limited to Hue-Saturation-Luminosity, Hue-Saturation-Value, or greyscale;
   determining a median color or intensity value for the pixels in each row, and creating at least a one dimensional array containing these values;
   determining a low-frequency variation in color value over the array and performing illumination correction and background subtraction;
   detecting a peaks or valley in the adjusted array corresponding to the test and control lines to be measured;
   determining a depth or height (intensity maxima/minima) and/or area (integrated intensity) of these peaks which correspond to detection lines of the test strip; and
   determining a qualitative presence of the selected indicia of the analyte by the number of peaks present, and/or a quantitative value of the selected indicia of the analyte by quantitative comparison of two or more peaks.

19. The system of claim 18, wherein the light source is an internal flash source of the smartphone.

20. The system of claim 18, wherein the light source is an light-emitting diode disposed in the smartphone accessory, further comprising a battery in the smartphone accessory to power the light-emitting diode.

21. The system of claim 18, wherein the system is smartphone platform-independent.

22. The system of claim 18, wherein the smartphone accessory is an unpowered component.

23. The system of claim 18, further comprising a colorimetric reactive test strip that is removeably disposable in the smartphone accessory.

24. The system of claim 23, wherein the colorimetric reactive test strip includes at least one test region and a control region.

25. The system of claim 23, wherein the colorimetric reactive test region is at least one of chemically colorimetric reactive, enzymatically colorimetric reaction, and gold nanoparticle colorimetrically reactive, including a lateral flow type immunoassay.

26. The system of claim 18, wherein the light diffuser is disposed on the at least a portion of a surface of the test strip is such a manner to provide diffuse illumination to a surface of the test strip.

* * * * *